(12) United States Patent
Spodsberg

(10) Patent No.: US 9,175,276 B2
(45) Date of Patent: Nov. 3, 2015

(54) POLYPEPTIDES HAVING ENDOGLUCANASE ACTIVITY AND POLYNUCLEOTIDES ENCODING SAME

(71) Applicants: Novozymes A/S, Bagsvaerd (DK); Novozymes Inc., Davis, CA (US)

(72) Inventor: Nikolaj Spodsberg, Bagsvaerd (DK)

(73) Assignee: Novozymes, Inc., Davis, CA (US)

(*) Notice: Subject to any disclaimer, the term of this patent is extended or adjusted under 35 U.S.C. 154(b) by 139 days.

(21) Appl. No.: 13/764,949

(22) Filed: Feb. 12, 2013

(65) Prior Publication Data

US 2014/0227739 A1    Aug. 14, 2014

(51) Int. Cl.
| | |
|---|---|
| C12N 15/00 | (2006.01) |
| C12S 3/00 | (2006.01) |
| C12P 21/00 | (2006.01) |
| A01H 5/00 | (2006.01) |
| C12N 9/42 | (2006.01) |
| C12P 19/14 | (2006.01) |
| C12P 19/02 | (2006.01) |
| C12P 21/02 | (2006.01) |

(52) U.S. Cl.
CPC ............... *C12N 9/2437* (2013.01); *C12P 19/02* (2013.01); *C12P 19/14* (2013.01); *C12P 21/02* (2013.01); *C12P 2203/00* (2013.01)

(58) Field of Classification Search
None
See application file for complete search history.

(56) References Cited

U.S. PATENT DOCUMENTS

| | | | | |
|---|---|---|---|---|
| 8,143,482 B2* | 3/2012 | Lassen et al. | ................. | 800/288 |
| 8,580,536 B2* | 11/2013 | McBrayer et al. | ............... | 435/41 |
| 2014/0230098 A1* | 8/2014 | Spodsberg | .................... | 800/298 |

OTHER PUBLICATIONS

Emanuelsson, 2007, Nat Protoc 2(4), 953-971.
Lee, 2011, Protein Sci 20, 1935-1940.
Leggioi, 2002, FEBS Lett 523, 103-108.
Petegem, 2002, Biochem Biophys Res Com 296, 161-166.

* cited by examiner

*Primary Examiner* — David H Kruse
*Assistant Examiner* — Jason Deveau Rosen
(74) *Attorney, Agent, or Firm* — Eric J. Fechter

(57) ABSTRACT

The present invention relates to isolated polypeptides having endoglucanase activity and polynucleotides encoding the polypeptides. The invention also relates to nucleic acid constructs, vectors, and host cells comprising the polynucleotides as well as methods of producing and using the polypeptides.

36 Claims, No Drawings

POLYPEPTIDES HAVING ENDOGLUCANASE ACTIVITY AND POLYNUCLEOTIDES ENCODING SAME

STATEMENT AS TO RIGHTS TO INVENTIONS MADE UNDER FEDERALLY SPONSORED RESEARCH AND DEVELOPMENT

This invention was made in part with Government support under Cooperative Agreement DE-FC36-08GO18080 awarded by the Department of Energy. The government has certain rights in this invention.

BACKGROUND OF THE INVENTION

1. Field of the Invention

The present invention relates to polypeptides having endoglucanase activity and polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of glucose linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol. Since glucose is readily fermented to ethanol by a variety of yeasts while cellobiose is not, any cellobiose remaining at the end of the hydrolysis represents a loss of yield of ethanol. More importantly, cellobiose is a potent inhibitor of endoglucanases and cellobiohydrolases. The accumulation of cellobiose during hydrolysis is undesirable for ethanol production.

The present invention provides polypeptides having endoglucanase activity and polynucleotides encoding the polypeptides.

SUMMARY OF THE INVENTION

The present invention relates to isolated polypeptides having endoglucanase activity selected from the group consisting of:

(a) a polypeptide having at least 85% sequence identity to the mature polypeptide of SEQ ID NO: 2, a polypeptide having at least 71% sequence identity to the mature polypeptide of SEQ ID NO: 4, a polypeptide having at least 74% sequence identity to the mature polypeptide of SEQ ID NO: 6, or a polypeptide having at least 75% sequence identity to the mature polypeptide of SEQ ID NO: 8;

(b) a polypeptide encoded by a polynucleotide that hybridizes under low, or medium, or medium-high, or high, or very high stringency conditions with (i) the mature polypeptide coding sequence of SEQ ID NO: 1, SEQ ID NO: 3, SEQ ID NO: 5, or SEQ ID NO: 7, (ii) the cDNA sequence thereof, or (iii) the full-length complement of (i) or (ii);

(c) a polypeptide encoded by a polynucleotide having at least 60% sequence identity to the mature polypeptide coding sequence of SEQ ID NO: 1, SEQ ID NO: 3, SEQ ID NO: 5, or SEQ ID NO: 7; or the cDNA sequence thereof;

(d) a variant of the mature polypeptide of SEQ ID NO: 2, SEQ ID NO: 4, SEQ ID NO: 6, or SEQ ID NO: 8 comprising a substitution, deletion, and/or insertion at one or more (e.g., several) positions; and (e) a fragment of the polypeptide of (a), (b), (c), or (d) that has endoglucanase activity.

The present invention also relates to isolated polypeptides comprising a catalytic domain selected from the group consisting of:

(a) a catalytic domain having at least 60% sequence identity to the catalytic domain of SEQ ID NO: 2 (for example, amino acids 37 to 348 of SEQ ID NO: 2), SEQ ID NO: 4 (for example, amino acids 90 to 402 of SEQ ID NO: 4), SEQ ID NO: 6 (for example, amino acids 94 to 420 of SEQ ID NO: 6), or SEQ ID NO: 8 (for example, amino acids 84 to 396 of SEQ ID NO: 8);

(b) a catalytic domain encoded by a polynucleotide having at least 60% sequence identity to the catalytic domain coding sequence of SEQ ID NO: 1 (for example, nucleotides 106-231, 288-407, 466-511, 564-612, 672-682, 741-766, 824-848, 905-954, 1007-1070, 1127-1150, 1211-1279, 1336-1488, 1544-1644, and 1700-1774 of SEQ ID NO: 1), SEQ ID NO: 3 (for example, nucleotides 381-503, 559-678, 734-779, 838-886, 940-950, 1010-1035, 1095-1119, 1179-1228, 1288-1351, 1410-1433, 1489-1557, 1624-1776, 1845-1948, and 2022-2096 of SEQ ID NO: 3), SEQ ID NO: 5 (for example, nucleotides 453-558, 608-759, 811-876, 927-1024, 1077-1160, 1212-1549, and 1600-1736 of SEQ ID NO: 5), or SEQ ID NO: 7 (for example, nucleotides 485-532, 592-685, 747-752, 804-925, 977-1093, 1143-1263, 1317-1418, 1471-1523, 1573-1682, 1740-1888, and 1941-1957 of SEQ ID NO: 7);

(c) a variant of a catalytic domain comprising a substitution, deletion, and/or insertion of one or more (several) amino acids of the catalytic domain of SEQ ID NO: 2, SEQ ID NO: 4, SEQ ID NO: 6, or SEQ ID NO: 8; and (d) a fragment of a catalytic domain of (a), (b), or (c), which has endoglucanase activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to processes for degrading a cellulosic material, comprising: treating the cellulosic material with an enzyme composition in the presence of a polypeptide having endoglucanase activity of the present invention. In one aspect, the processes further comprise recovering the degraded or converted cellulosic material.

The present invention also relates to processes of producing a fermentation product, comprising: (a) saccharifying a cellulosic material with an enzyme composition in the presence of a polypeptide having endoglucanase activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having endoglucanase activity of the present invention. In one aspect, the fermenting of the cellulosic material produces a fermentation product. In another aspect, the processes further comprise recovering the fermentation product from the fermentation.

The present invention also relates to a polynucleotide encoding a signal peptide comprising or consisting of amino acids 1 to 22 of SEQ ID NO: 2, amino acids 1 to 23 of SEQ ID NO: 4, amino acids 1 to 20 of SEQ ID NO: 6, or amino acids 1 to 19 of SEQ ID NO: 8, which is operably linked to a gene encoding a protein; nucleic acid constructs, expression vectors, and recombinant host cells comprising the polynucleotides; and methods of producing a protein.

SEQUENCES OF THE INVENTION

*Hohenbuehelia mastrucata* Strain NN009379 Genomic Nucleotide Sequence (SEQ ID NO: 1):

Exons/Introns (in Base Pairs) of SEQ ID NO: 1:

| Exon 1 | 1-231 bp |
|---|---|
| Intron 1 | 232-287 bp |
| Exon 2 | 288-407 bp |
| Intron 2 | 408-465 bp |
| Exon 3 | 466-511 bp |
| Intron 3 | 512-563 bp |
| Exon 4 | 564-612 bp |
| Intron 4 | 613-671 bp |
| Exon 5 | 672-682 bp |
| Intron 5 | 683-740 bp |
| Exon 6 | 741-766 bp |
| Intron 6 | 767-823 bp |
| Exon 7 | 824-848 bp |
| Intron 7 | 849-904 bp |
| Exon 8 | 905-954 bp |
| Intron 8 | 955-1006 bp |
| Exon 9 | 1007-1070 bp |
| Intron 9 | 1071-1126 bp |
| Exon 10 | 1127-1150 bp |
| Intron 10 | 1151-1210 bp |
| Exon 11 | 1211-1279 bp |
| Intron 11 | 1280-1335 bp |
| Exon 12 | 1336-1488 bp |
| Intron 12 | 1489-1543 bp |
| Exon 13 | 1544-1644 bp |
| Intron 13 | 1645-1699 bp |
| Exon 14 | 1700-1777 bp |

```
   1   ATGCTGTCCA GGTCACTCTT TGTTTCGTTG GCTATATTCG CTTCGGTGGC TACACCCGCT GCTGCGGCTG TTCTGCCACC

81   TACCTCCACC ACAACTGCCG CAGATGCCTG CCCCAACGCC ACGAAATTCA AGTTCTTTGG CGTCAACGAA TCTGGCGCCG

161   AATTTGGCAA CCAAAACATT CCTGGTGTGC TTGGAACAGA CTACACCTGG CCATCGCCGT CCTCTATCGA CGTATGTATC

241   AAAAGTGACG ACACGATGGA CAGTAATCTG ATGTTTCTGG GCGTTAGTTC TTCACCGACA AAGGCTTCAA CGCCTTCCGC

321   ATTCCTTTCC AGCTTGAGCG TCTCAGTCCG CCAGCGACTG GTCTCACAGG CGCATTCGAT GCGACATACC TAAGTGGTCT

401   CCAAACGGTG GGTAACCTAT TATTTACGAT CCTAACTCTG GAGCATGACA GATTCCATTC ACTAGATTGT TGAATACATC

481   ACGAGCAAAG GCGCATTTGC TGCTATCGAG CGTATGTATC CTTTACCGCT ACCAAAGTGT ATTCAACTAA ACCCTAATGA

561   TAGCCCACAA CTTTATGATC TACAATGGCG CCCAAATTAC TTCTACCGCG GAGTAAGTGG GAATACATTA TTTCCTTGTC

641   TTTACTGACG CTTTTGATTT TGCGCAAATA GTTTCGCCAC ATGTTCGTAT TCAACCTAAG TCTATCTCAG ATTGAATTAT

721   TTGCTCATTC ACAAGCACAG TCTGGCAGAA CCTAGCCACG ATCTTCGTAC GTCATGTCAT GCTCGCCCGT GTCACCCTAC

801   CAGGTACTCA GGTCATGCTT CAGAAAGATA ACGCAAACGT CATTTTCGGT ATGAACAGGG CAGAGACCCG ACTGGCATAA

881   GATGACAATC TCCGCATTTT TCAGATATAA TCAACGAGCC TCATGACATG CCTGCCACTA CTGTGTTCGA TCTGGTACGC

961   CGTATGTATC CGCGCAAAAC AGGACATTCC TCGTTCATGA TTATAGAATC AAGCCGCGGT GAATGGTATC CGCGCCAGCG

1041   GAGCTACGTC ACAGTTGATA CTCGTCGAGG GTATGCTGTT CTTGCGGTCA TCTACATGTA ATGGATCTAA CACAGCGGTT

1121   ATCAAGGAAC ATCCTGGACT GGCGCGTGGA GTAGGTCACA GCTCACAACC ATGTCACAAT ATCGGGTCCG CTGAAAATTT

1201   CTCTGCTCAG CATGGATCAC TTCCGGCAAC GGCGATGCCT TCGTGGGCAT TTCTGATCCT AACGATAACA TTGCCATTGG

1281   TGGGATCCTT ATTGGTTCAG CTCGAACGCA TCAAAGCTCA ACTCCGGTTT CGTAGAGATG CACCAATACC TCGACTCTGA

1361   TGGCTCTGGG ACATCCGAGA TTTGTGTTTC GCCTACCATC GGTGCCGAGC GACTCCAAGC TGCCACGGAC TGGCTCAAGG

1441   CCAATAACCT GAAAGGTTTC CTTGGCGAGA TTGGCGCGGG ATCAAATGGT ATGAGGTCCA TCTTCTTTAA TAGCCCGACT

1521   TACTAAGCTA CCTATTCTGC CAGCCGACTG TATCAGTGCT GTCACTGGCG CGTTCTGCGC TATGCAGCAG TCTGGAGTGT

1601   GGATCGGCGC TCTGTGGTGG GCTGCTGGGC CTTGGTGGGG TGACGTCAGT GCATAATCAA GCCTTGCATG ACTTGTGATG

1681   CTGATCTTCT TGTCTTTAGT ACTACCAGTC TATCGAGCCT CCCAATGGAC CTGCCCTCGC CGAGATTCTC CCTCAAGCTC

1761   TCGAGCCTTT CCTTTAA
```

Features (in Base Pairs) of SEQ ID NO: 1:

| | |
|---|---|
| Signal Peptide | 1-63 bp |
| Linker | 64-105 bp |
| Endoglucanase catalytic site | 106-231, 288-407, 466-511, 564-612, 672-682, 741-766, 824-848, 905-954, 1007-1070, 1127-1150, 1211-1279, 1336-1488, 1544-1644, 1700-1774 bp |
| Stop codon | 1775-1777 bp |

Protein Sequence of *Hohenbuehelia mastrucata* Strain NN009379 Protein (SEQ ID NO: 2):

```
  1 MLSRSLFVSL AIFASVATPA AAVLPPTST TTAADACPNA TKFKFFGVNE SGAEFGNQNI

61 PGVLGTDYTW PSPSSIDFFT DKGFNAFRIP FQLERLSPPA TGLTGAFDAT YLSGLQTIVE

121 YITSKGAFAA IEPHNFMIYN GAQITSTADF ATFWQNLATI FKDNANVIFD IINEPHDMPA

181 TTVFDLNQAA VNGIRASGAT SQLILVEGTS WTGAWTWITS GNGDAFVGIS DPNDNIAIEM

241 HQYLDSDGSG TSEICVSPTI GAERLQAATD WLKANNLKGF LGEIGAGSNA DCISAVTGAF

301 CAMQQSGVWI GALWWAAGPW WGDYYQSIEP PNGPALAEIL PQALEPFL
```

Features of SEQ ID NO: 2 (amino acid positions):

| | |
|---|---|
| Signal Peptide | 1-22 |
| Linker | 23-36 |
| Endoglucanase catalytic site | 37-348 |

Signal Peptide Sequence of SEQ ID NO: 2:

MLSRSLFVSLAIFASVATPAAA

*Hohenbuehelia mastrucata* Strain NN009379 Genomic Nucleotide Sequence (SEQ ID NO: 3):

```
   1   ATGCGGTCGG CACTCTCTGC GTTCGCCTGT TTGGCGGTCT TGACATCCCT CGTCGCTCCG GCGACTGCGG TGGCTGTCTA

81   CGGACAATGC GGTGTAAGTA ATCTTTCAAT TTAAGTCACG CAAGGCTTTA TCGAATGTAC TTGCATTTTT AAGGGCATCG

161   GTTACACTGG CTCTACCGTC TGCGATGCGG GCTCGTACTG CAAGTACACC AATGACTGTA AGTATCGAAT ATTGTATGCT

241   TGGGACCGTC TCTAATAATC TCACCAAAAG GGTACTCCCA ATGTCTACCT GGAAGCGACC CAAATGCACC TACGTCAACC

321   TCCGTGCCTG CTACATCATC CTCGTCGTCG ACATCTACCG CACCTGCCCC AAGTGGCAGC TGCGCCAACA GGACAAAGTT

401   CAAGTACTTC GGTGTCAACG AGTCTGGCGC CGAGTTCGGC AACCAGAATA TCCCTGGTGT CCTTGGTACC GACTACACAT

481   GGCCGTCGCC GTCGTCCATC GACGTGAGTG GGCTATCCAT CTCATCAATC TTCATCGGCT GACCAATACC TTGGGCAGTA

561   CTTCGTCGGC AAGGGCTTCA ACATCTACCG CATTCCCTTC CAGCTTGAGC GTCTCAGCCC GCCAGCGCAG GGCCTTACTG

641   GCTCCTTTGA CGCAACCTAC TTGGCTGGTC TGCAAACTGT GAGTTTCTTG TTGACAGTAC CTCGAGCATC GAAGACTGAA

721   TGCGCGATGC CAGATTGTTA ACTACATCAC AAGCAAGGGA GCGTATGCTG CCATTGAACG TGAGCATCTC TTGCTATAGT

801   TGTCAAACGC CTGTGGCTCA AGACGCACTT TGCTTAGCCC ACAACTTCAT GAGCTACAAC GGTGCTCAGA TCACCTCAAC

881   GACCAAGTAA GTGAACTTTT CGGTACACGC AGCGACAGCA TGCTTATTTA CGTATACAGC TTTGCGACCT GTGCGTTTAA
```

-continued

```
 961  ACATAGTTAT CAGGAAAGAG TTGTTCACTG GCTGACGCGC TGATCACAGG GTGGAAGAAC CTTGCCACTG TCTTCGTGAG
1041  TATCGTCTTT CATTACCTGG TGTGTTCGAA TAAGCTTACT CACCTGTGGC GTAGAAAAGC AACAATAACG TCATTTTCGG
1121  TGAGCGATTC GCTGCACAAT TTTGATGAAT ACATTCTGAA TGTATTTGAT GTGTATAGAT ATTATGAACG AGCCCAACGG
1201  CATCGCTGCA AGCACTGTCT TCAGTCTCGT GTGTAGCGAC TTCCAGACTT GAGATACGCT ATAACTCACT ATCGTCATTC
1281  ATTGCAGAAC CAAGCTGCAG TCAACGGTAT TCGCGCTTCT GGTGCTACCA CACAGCTCAT CCTTGTAGAA GGTCTGTTAT
1361  CCCTATCTTA ATCGAAGAGC AGCTCTCGCT GATGATGCAT ACTGTATAGG AACTGCCTGG ACCGGAGCTT GGAGTGCGTT
1441  TTGTACACCC AGGGTCCACG TATCCTGAAC TAATATATTC AATTTTAGGC TGGCAATCTT CTGGCAATGC TGCCGCCTTC
1521  GTTGCCCTCA CGGATCCCAA CAACAACATC GCCATCGGTG CGTCGCTTTA GCCTCTGCCT TCTCGTCCTG ATCTGGTTGG
1601  CTGAATACTC CCTCTGCGCG TAGAAATGCA CCAGTACCTC GACTCCGACA GCTCCGGCAC ATCCCCGACC TGTGTATCCT
1681  CCACCATCGG CGTCGAGCGC ATCCAAGCCG CCACGGCGTG GCTCCAACAG AACAAGCTCA AGGGCTTCCT CGGGGAGATG
1761  GGCGCGGGCT CGAACAGTGC GTGTGCTCAC CAGCATTTTT ACTTTTGCCA GGTTTCTCAC GTGTGTTCGG TTCGCTTTTG
1841  GCAGGCGTCT GCATCGATGC TATCAAGGGC GCGCTCTGCC ATATGCAGCA GGCTGGCGGT ACATGGATCG GGTTCCTCTG
1921  GTGGGCGGCC GGTCCCTGGT GGGGAACTGT GAGTGCTCTG TGGTCTTGTC CTTGTGCAGC TGCGAGGATG GACGGTGCTA
2001  ACGCGTGCTC TTTGATGGCA GTACTTCCAA TCGATCGAGC CACCCAATGG TGCATCGATC TCGCAGGTCC TCCCACAGGC
2081  TCTCATACCG TTCTTGTAG
```

Exons/Introns (in Base Pairs) of SEQ ID NO: 3:

| | |
|---|---|
| Exon 1 | 1-93 bp |
| Intron 1 | 94-153 bp |
| Exon 2 | 154-217 bp |
| Intron 2 | 218-270 bp |
| Exon 3 | 271-503 bp |
| Intron 3 | 504-558 bp |
| Exon 4 | 559-678 bp |
| Intron 4 | 679-733 bp |
| Exon 5 | 734-779 bp |
| Intron 5 | 780-837 bp |
| Exon 6 | 838-886 bp |
| Intron 6 | 887-939 bp |
| Exon 7 | 940-950 bp |
| Intron 7 | 951-1009 bp |
| Exon 8 | 1010-1035 bp |
| Intron 8 | 1036-1094 bp |
| Exon 9 | 1095-1119 bp |
| Intron 9 | 1120-1178 bp |
| Exon 10 | 1179-1228 bp |
| Intron 10 | 1229-1287 bp |
| Exon 11 | 1288-1351 bp |
| Intron 11 | 1352-1409 bp |
| Exon 12 | 1410-1433 bp |
| Intron 12 | 1434-1488 bp |
| Exon 13 | 1489-1557 bp |
| Intron 13 | 1558-1623 bp |
| Exon 14 | 1624-1776 bp |
| Intron 14 | 1777-1844 bp |
| Exon 15 | 1845-1948 bp |
| Intron 15 | 1949-2021 bp |
| Exon 16 | 2022-2099 bp |

Features (in Base Pairs) of SEQ ID NO: 3:

| | |
|---|---|
| Signal Peptide | 1-69 bp |
| Cellulose Binding Module (CBM 1) | 70-93, 154-217, 271-290 bp |
| Linker | 291-380 bp |
| Endoglucanase catalytic site | 381-503, 559-678, 734-779, 838-886, 940-950, 1010-1035, 1095-1119, 1179-1228, 1288-1351, 1410-1433, 1489-1557, 1624-1776, 1845-1948, 2022-2096 bp |
| Stop codon | 2097-2099 bp |

Protein Sequence of *Hohenbuehelia mastrucata* Strain NN009379 Protein (SEQ ID NO: 4):

```
  1  MRSALSAFAC LAVLTSLVAP ATAVAVYGQC GGIGYTGSTV CDAGSYCKYT NDWYSQCLPG
 61  SDPNAPTSTS VPATSSSSST STAPAPSGSC ANRTKFKYFG VNESGAEFGN QNIPGVLGTD
121  YTWPSPSSID YFVGKGFNTF RIPFQLERLS PPAQGLTGSF DATYLAGLQT IVNYITSKGA
181  YAAIEPHNFM SYNGAQITST TNFATWWKNL ATVFKSNNNV IFDIMNEPNG IAASTVFSLN
241  QAAVNGIRAS GATTQLILVE GTAWTGAWSW QSSGNAAAFV ALTDPNNNIA IEMHQYLDSD
301  SSGTSPTCVS STIGVERIQA ATAWLQQNKL KGFLGEMGAG SNSVCIDAIK GALCHMQQAG
361  GTWIGFLWWA AGPWWGTYFQ SIEPPNGASI SQVLPQALIP FL
```

Features of SEQ ID NO: 4 (Amino Acid Positions):

| | |
|---|---|
| Signal Peptide | 1-23 |
| Cellulose Binding Module (CBM 1) | 24-59 |
| Linker | 60-89 |
| Endoglucanase catalytic site | 90-402 |

Signal Peptide Sequence of SEQ ID NO: 4:

MRSALSAFACLAVLTSLVAPATA

*Hohenbuehelia mastrucata* Strain NN009379 Genomic Nucleotide Sequence (SEQ ID NO: 57):

```
   1  ATGAAGTCTC CATACTTTGC TATTCTCTTG GCCACTGCGC TTCGTGTCCG CGGTCAAGGC GCTTTGTACA CACAATGTGC
  81  GTTCCGCTTG ACGTTTCCCA AGCCAAGCCC ATTTAACATC CTGGTCCCTA ACAGGTGGTG GCGTTGTAAG TCGTATTCGT
 161  CCTATTATAC GCCTACCAAA TATTAGTGAA GCTGATATTC ATTCAATAGG CTGGACAGGA AGCGACAACT TGCGTCGCTG
 241  GGGCTGTATG CTCCAAACTG AATGACTGTG GGTTCATTTC GACGATAAGT ATTTCGTAAG GCTGATTGAG TTACCCAGAC
 321  TATTCGCAGT GCATTCCAGG AGCAGCCGCC CCGTCTTCAT CTGTGTCATC TGTGTCATCT TCCGCTGCGC CGACGAAGGT
 401  GTCAACTTCT GTTGCGTCGA CCGGAACAAC CACACCGCCG CCAACTGCAG GAAAGCTCCG TTTTACTGGC GTCAATATTG
 481  CCGGATTCGA CTTTGGTTGC TCTACCGACG GGACATGCAA CGCCAGCGGT GCCTACCCAC CTCTGCTTGA GTATTACGGC
 561  AAGTTACGGG TTTCTTCCTG CTGGGACACT TGCTGAGTGT ATCTTAGGCG CTGATGGAGA AGGCCAAATG AAGCACTTTG
 641  TCAATGATGA TGGTTTTAAC ACTTTCCGCC TGCCCGTCGG CTGGCAGTTT TTGACAAACG ATGTGCTCAC CGGCACTATC
 721  AACGAGGATA ACTGGGTCAA GTACGATGCT TTGGTCCAAG TAGGTGCCGC TCATTCCATC TGTTGTGGGG GTTTCTGACC
 801  GATTTTGTAG GCCTGTCTTA ACACGGGAGC ATACTGCATC GTTGACGTAC ATAACTATGC GCGGTGGAAT ACCAAGGTCC
 881  GTTCAAGGTG GCCTATTCTT AAAGCTTGGT TCTGATTGTC GTTCAGATTA TTGGACAGGG CGGCCCAAGC AACGAGATAT
 961  TCGCCGACCT TTGGGCATCG ATTGCTACAA AATACAAGGA TAATACGAAA ATTATCTTCG GCATGTAAGC GTTATATTTG
1041  GCCGTCCCCA GTATGCACTC TAAGCTGGCA CCCCAGAATG AACGAACCTC ATGATGTCCC CGACATCAAA ATGTGGGCTG
1121  CATCCGTCCA GGCTGCTGTT ACAGCAATCC GGAACGCCGG GTTGGTGGAA TTTCTACGAG TTCGTTAGTT CTGCAGCTGA
1201  TGTTTCCATA GAGCGACGAG CCACATCCTA CTTCTTCCCG GCAACGACTG GACATCTGCG GCAGCCTTCA TCCCTAACGG
1281  CTCTGCCGAC GCGCTCTCAA AGGTCACCAA CCCGGATGGC AGCGTGACGA ACCTTGTCTT CGACGTCCAC AAGTATCTCG
1361  ACAGCGACAA CAGCGGCACG CACGCCGAAT GCGTGACGAA CAATATCGCC GAAGCCTGGC AACCTCTCGG GGACTGGCTC
1441  CGTGCTAATG GACGCCAAGC TTTCAACACC GAGACAGGCG GCGGCAACAC CGCATCGTGT GTAACCTATC TATGCGAGCA
1521  GATCGCGTAC CAGAATGCCA ACTCCGATGG TAAGTTGCTC CGAAGAACGT CATTGGCGTT GTTTCTGATC AGTCTGCAGT
1601  TTACCTCGGC TATGTTGGCT GGTCAGCAGG TAACTTCTAC CATGGATATG TCCTAGACGA GGTCCCTACA GGGAGCGGGT
1681  CGACTTGGAC GGACACAATG CTGGTCGCTA GCTGCTTGGC CCCGAACGCG GCAAATAG
```

Exons/Introns (in Base Pairs) of SEQ ID NO: 5:

| | |
|---|---|
| Exon 1 | 1-76 bp |
| Intron 1 | 77-134 bp |
| Exon 2 | 135-145 bp |
| Intron 2 | 146-209 bp |
| Exon 3 | 210-267 bp |
| Intron 3 | 268-318 bp |
| Exon 4 | 319-558 bp |
| Intron 4 | 559-607 bp |
| Exon 5 | 608-759 bp |
| Intron 5 | 760-810 bp |
| Exon 6 | 811-876 bp |
| Intron 6 | 877-926 bp |
| Exon 7 | 927-1024 bp |
| Intron 7 | 1025-1076 bp |
| Exon 8 | 1077-1160 bp |
| Intron 8 | 1161-1211 bp |
| Exon 9 | 1212-1549 bp |
| Intron 9 | 1550-1599 bp |
| Exon 10 | 1600-1739 bp |

Features (in Base Pairs) of SEQ ID NO: 5:

| | |
|---|---|
| Signal Peptide | 1-60 bp |
| Cellulose Binding Module (CBM 1) | 61-76, 135-145, 210-267, 319-338 bp |
| Linker | 339-452 bp |
| Endoglucanase catalytic site | 453-558, 608-759, 811-876, 927-1024, 1077-1160, 1212-1549, 1600-1736 bp |
| Stop codon | 1737-1739 bp |

Protein Sequence of *Hohenbuehelia mastrucata* Strain NN009379 Protein (SEQ ID NO: 6):

```
  1 MKSPYFAILL ATALRVRGQG ALYTQCGGVG WTGATTCVAG AVCSKLNDYY SQCIPGAAAP
 61 SSSVSSVSSS AAPTKVSTSV ASTGTTTPPP TAGKLRFTGV NIAGFDFGCS TDGTCNASGA
121 YPPLLEYYGA DGEGQMKHFV NDDGFNTFRL PVGWQFLTND VLTGTINEDN WVKYDALVQA
181 CLNTGAYCIV DVHNYARWNT KIIGQGGPSN EIFADLWASI ATKYKDNTKI IFGIMNEPHD
241 VPDIKMWAAS VQAAVTAIRN AGATSHILLL PGNDWTSAAA FIPNGSADAL SKVTNPDGSV
301 TNLVFDVHKY LDSDNSGTHA ECVTNNIAEA WQPLGDWLRA NGRQAFNTET GGGNTASCVT
361 YLCEQIAYQN ANSDVYLGYV GWSAGNFYHG YVLDEVPTGS GSTWTDTMLV ASCLAPNAAK
```

Features of SEQ ID NO: 6 (Amino Acid Positions):

| | |
|---|---|
| Signal Peptide | 1-20 |
| Cellulose Binding Module (CBM 1) | 21-55 |
| Linker | 56-93 |
| Endoglucanase catalytic site | 94-420 |

Signal Peptide Sequence of SEQ ID NO: 6:

MKSPYFAILLATALRVRGQG

*Hohenbuehelia mastrucata* Strain NN009379 Genomic Nucleotide Sequence (SEQ ID NO: 7):

```
   1 ATGAAATATA TTGCAACCAC TGTGGCACTT TTTGCCGCCC TCACCTCTGT TCGCGCGCAG CAACCAGTGA GTACGCAGGC
  81 ATAATGTATT CATCTCATCG CTAATAGCAT ATTATTATGC ACAAAATAGT TGTATGCTCA ATGTAAGTTC ACCTGTCAGT
 161 AATCCGTGTA ATAGGCTTTC TGAATATCCT TGGTGTGCTC TTCAGGCGGT GGAATTGGAT GGTGTACGTT CAACGTAATG
 241 TGGTCATCCT TACGCTGTAC TTATTATTCG TTAGCTGGAG GGACTACCTG TGTCTCAGGA GCATCTTGCA GCAAGCTGAA
 321 TGACTGTGCG CTGCTTCGTT TCGTTGCCAC AACATTGTTA CATCTTATCT TTTTTCTTTT CAGATTATTC TCAATGCTTG
 401 CCTGGCGCGG CTGCACCGAC CTCTTCGACC CCACCCCCA CTAGTAGTAC AGGATCGTCG CCGGCACCCA CCGCCTCCAG
 481 CGTGCTGCCT TTTGTTGGCG GCGTCAACAT GGCTGGTTAC GACTTTTCCT CCGTACGTTC AAACAAATGA AGACAAAGGT
 561 ATCCTGTTTT GAACTGAAGG TAATCTTTTA GGCTACCGAC GCATCTTGCA AGGACGACAG TACCGACCCG CCCGTCTCTC
 641 AGTTCTCTCA CTTTGCTCAG CAAGGCGTCA ACATTTTCCG TATTCGTGCG TTCCGTCTTA TTCCGTCTTA TGAATAACTG
 721 ACTCAACGAC AATTCGTTGA TGTTAGCCTT TGGTACGTTT AGTACTTACC TGAATTGCTT TTGTTCGTTA ATCGTTGTTG
 801 TAGCTTGGCA ATTGATGACG CCTACTCTTG GAGGGACGAT TGACCCGACG TTTGCCGCCC GCTACGACCG AACTGTGCAA
 881 GCTGCACTGA ACTCGAATTC CAAGGCATAC GTTATTATTG ATGTTGTATG TCCATCATTC CACTTTTTGC GAGGTTTTTA
 961 TTGATCAGTC GTCAAGCACA ATTACGCTCG CTGGAACGGT GCCGTCATTG CCCAAGGCGG TCCCACTGAT GCGCAGTATG
1041 CCAGTCTATG GTCTCAGCTT GCAGCCAAGT ATGCCAGCAA CTCGCGCATA ATCGTGAGTC AACGTTTATA GGCTGCGGTT
1121 CTGCTTTTTC AATCATTCGT AGTTTGGCAT CATGAACGAG CCCCATGATG TCCCGAACAT CGCAACTTGG GCGAACTCTG
1201 TTCAGGCCGC AGTGAACGCA ATTCGTGCGG CTGGCGCAAC TTCGCAAGTC ATTCTTCTTC CCGGTACGTC GAGCGCACCG
1281 TTTCACTGTT CACAAATTTC CTCATACCGG CGGTAGGCTC TAGCTGGTCC AGCGCTCAGG CCTTCCCTAC CGAAGCTGGC
1361 CCTTACCTCG TGAAGGTTAC GGATCCTGCT GGTGGAACGA GCAAACTCAT CTTCGATGGT AATGCAATAT TTACTTTGGA
1441 CTAATGGCCC GAAGACTGAC TGCCTGCTAG TCCACAAGTA CCTTGACAGT GACAATAGCG GGACTCACGC TGACTGTACG
1521 ACCGTAAGTC AAAACTTTAG CATGCTTAAA CCATTCCTCA CGTGCCGAAT AGGACAATGT CCCAGTTTTC CAGACACTCG
1601 TGAACTTCCT GAAGGCCAAT GGGAACCGTC AGGCTCTCCT CAGCGAAACT GGCGGTGGCA CACCTCATCC TGCTTCACT
1681 GCGTTCGTGC TAGCCTATAA CGAGACTTCC GTATCCTTAC TCACATGTTC TTATAACAGA CTCAATTCAG AACTTGCTTT
1761 CGTCAAGTCA AACTTCCCAA CCCTTGTGGG CTTCACGGTT TGGAGTGCTG GTGCCTTCGA CACAACTTAC ATCCTAACGC
1841 TGACGCCGAA TCCTGACGGC TCTGACCAAC CTCTCTGGAT CCAAGCTGGT AAGCGCAGTT GATTCTGAAC TCCAATAATC
1921 AAGACTTACG TTTTTTTTAG TCCGCCCCAA CCTGCCTTGA
```

Exons/Introns (in Base Pairs) of SEQ ID NO: 7:

| Exon 1 | 1-66 bp |
|---|---|
| Intron 1 | 67-129 bp |
| Exon 2 | 130-142 bp |
| Intron 2 | 143-205 bp |
| Exon 3 | 206-223 bp |
| Intron 3 | 224-274 bp |
| Exon 4 | 275-325 bp |
| Intron 4 | 326-383 bp |
| Exon 5 | 384-532 bp |
| Intron 5 | 533-591 bp |
| Exon 6 | 592-685 bp |
| Intron 6 | 686-746 bp |
| Exon 7 | 747-752 bp |
| Intron 7 | 753-803 bp |
| Exon 8 | 804-925 bp |
| Intron 8 | 926-976 bp |
| Exon 9 | 977-1093 bp |
| Intron 9 | 1094-1142 bp |
| Exon 10 | 1143-1263 bp |
| Intron 10 | 1264-1316 bp |
| Exon 11 | 1317-1418 bp |
| Intron 11 | 1419-1470 bp |
| Exon 12 | 1471-1523 bp |
| Intron 12 | 1524-1572 bp |
| Exon 13 | 1573-1682 bp |
| Intron 13 | 1683-1739 bp |
| Exon 14 | 1740-1888 bp |
| Intron 14 | 1889-1940 bp |
| Exon 15 | 1941-1960 bp |

Features (in Base Pairs) of SEQ ID NO: 7:

| Signal Peptide | 1-57 bp |
|---|---|
| Cellulose Binding Module (CBM 1) | 58-66, 130-142, 206-223, 275-325, 384-403 bp |
| Linker | 404-484 bp |
| Endoglucanase catalytic site | 485-532, 592-685, 747-752, 804-925, 977-1093, 1143-1263, 1317-1418, 1471-1523, 1573-1682, 1740-1888, 1941-1957 bp |
| Stop codon | 1958-1960 bp |

Protein Sequence of *Hohenbuehelia mastrucata* Strain NN009379 Protein (SEQ ID NO: 8):

```
  1 MKYIATTVAL FAALTSVRAQ QPLYAQCGGI GWSGGTTCVS GASCSKLNDY YSQCLPGAAA

61 PTSSTPTPTS STGSSPAPTA SSVLPFVGGV NMAGYDFSSA TDGSFKDDST DPPVSQFSHF

121 AQQGVNIFRI PFAWQLMTPT LGGTIDPTFF ARYDRTVQAA LNSNSKAYVI IDVHNYARWN

181 GAVIAQGGPT DAQYASLWSQ LAAKYASNSR IIFGIMNEPH DVPNIATWAN SVQAAVNAIR

241 AAGATSQVIL LPGSSWSSAQ AFPTEAGPYL VKVTDPAGGT SKLIFDVHKY LDSDNSGTHA

301 DCTTDNVPVF QTLVNFLKAN GNRQALLSET GGGNTSSCFT ALNSELAFVK SNFPTLVGFT

361 VWSAGAFDTT YILTLTPNPD GSDQPLWIQA VRPNLP
```

Features of SEQ ID NO: 8 (Amino Acid Positions):

| Signal Peptide | 1-19 |
|---|---|
| Cellulose Binding Module (CBM 1) | 20-56 |
| Linker | 57-83 |
| Endoglucanase catalytic site | 84-396 |

Signal Peptide Sequence of SEQ ID NO: 8:

MKYIATTVALFAALTSVRA

DEFINITIONS

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

In one aspect, the polypeptides of the present invention have at least 20%, e.g., at least 40%, at least 50%, at least 60%, at least 70%, at least 80%, at least 90%, at least 95%, or at least 100% of the endoglucanase activity of the mature polypeptide of SEQ ID NO: 2, SEQ ID NO: 4, SEQ ID NO: 6, or SEQ ID NO: 8.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methyl-glucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1-4)-xylooligosaccharides to remove successive D-xylose residues from non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teen et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581. In the present invention, the Tomme et al. method can be used to determine cellobiohydrolase activity.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl(feruloyl) groups from esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide; wherein the fragment has endoglucanase activity. In one aspect, a fragment contains at least 20 amino acid residues, e.g., at least 30 to 347 amino acid residues or at least 50 to 340, 80 to 320, 100 to 300, 150 to 280, or 200 to 250, or any number in between, amino acid residues of SEQ ID NO: 2. In another aspect, a fragment contains at least 20 amino acid residues, e.g., at least 30 to 401 amino acid residues or at least 50 to 390, 80 to 370, 100 to 350, 150 to 300, or 200 to 250, or any number in between, amino acid residues of SEQ ID NO: 4. In another aspect, a fragment contains at least 20 amino acid residues, e.g., at least 30 to 419 amino acid residues or at least 50 to 410, 80 to 390, 100 to 350, 150 to 300, or 200 to 250, or any number in between, amino acid residues of SEQ ID NO: 6. In another aspect, a fragment contains at least 20 amino acid residues, e.g., at least 30 to 395 amino acid residues or at least 50 to 390, 80 to 370, 100 to 350, 150 to 300, or 200 to 250, or any number in between, amino acid residues of SEQ ID NO: 8.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 23 to 348 of SEQ ID NO: 2 based on the SignalP program (Nielsen et al., 1997, *Protein Engineering* 10:1-6) that predicts amino acids 1 to 22 of SEQ ID NO: 2 are a signal peptide. In another aspect, the mature polypeptide is amino acids 1 to 348 of SEQ ID NO: 2. In another aspect, the mature polypeptide is amino acids 24 to 402 of SEQ ID NO: 4 based on the SignalP program that predicts amino acids 1 to 23 of SEQ ID NO: 4 are a signal peptide. In another aspect, the mature polypeptide is amino acids 1 to 402 of SEQ ID NO: 4. In another aspect, the mature polypeptide is amino acids 21 to 420 of SEQ ID NO: 6 based on the SignalP program that predicts amino acids 1 to 20 of SEQ ID NO: 6 are a signal peptide. In another aspect, the mature polypeptide is amino acids 1 to 420 of SEQ ID NO: 6. In another aspect, the mature polypeptide is amino acids 20 to 396 of SEQ ID NO: 8 based on the SignalP program that predicts amino acids 1 to 19 of SEQ ID NO: 8 are a signal peptide. In another aspect, the mature polypeptide is amino acids 1 to 396 of SEQ ID NO: 8. It is known in the art that a host cell may produce a mixture of two or more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having endoglucanase activity. In one aspect, the mature polypeptide coding sequence is nucleotides 64 to 1774 of SEQ ID NO: 1 or the cDNA sequence thereof based on the SignalP program (Nielsen et al., 1997, supra) that predicts nucleotides 1 to 63 of SEQ ID NO: 1 encode a signal peptide. In another aspect, the mature polypeptide coding sequence is nucleotides 1 to 1774 of SEQ ID NO: 1 or the cDNA sequence thereof. In another aspect, the mature polypeptide coding sequence is nucleotides 70 to 2096 of SEQ ID NO: 3 or the cDNA sequence thereof based on the SignalP program that predicts nucleotides 1 to 69 of SEQ ID NO: 3 encode a signal peptide. In another aspect, the mature polypeptide coding sequence is nucleotides 1 to 2096 of SEQ ID NO: 3 or the cDNA sequence thereof. In another aspect, the mature polypeptide coding sequence is nucleotides 61 to 1736 of SEQ ID NO: 5 or the cDNA sequence thereof based on the SignalP program that predicts nucleotides 1 to 60 of SEQ ID NO: 5 encode a signal peptide. In another aspect, the mature polypeptide coding sequence is nucleotides 1 to 1736 of SEQ ID NO: 5 or the cDNA sequence thereof. In another aspect, the mature polypeptide coding sequence is nucleotides 58 to 1957 of SEQ ID NO: 7 or the cDNA sequence thereof based on the SignalP program that predicts nucleotides 1 to 57 of SEQ ID NO: 7 encode a signal peptide. In another aspect, the mature polypeptide coding sequence is nucleotides 1 to 1957 of SEQ ID NO: 7 or the cDNA sequence thereof.

Catalytic domain: The term "catalytic domain" means the portion of an enzyme containing the catalytic machinery of the enzyme.

Cellulose binding domain: The term "cellulose binding domain" means the portion of an enzyme that mediates binding of the enzyme to amorphous regions of a cellulose substrate. The cellulose binding domain (CBD) is found either at the N-terminal or at the C-terminal extremity of an enzyme. A CBD is also referred to as a cellulose binding module or CBM. In one embodiment the CBM is amino acids 24 to 59 of SEQ ID NO: 4. In one embodiment the CBM is amino acids 21 to 55 of SEQ ID NO: 6. In one embodiment the CBM is amino acids 20 to 56 of SEQ ID NO: 8. The CBM is separated from the catalytic domain by a linker sequence. The linker is in one embodiment amino acids 23 to 36 of SEQ ID NO: 2. The linker is in one embodiment amino acids 60 to 89 of SEQ ID NO: 4. The linker is in one embodiment amino acids 56 to 93 of SEQ ID NO: 6. The linker is in one embodiment amino acids 57 to 83 of SEQ ID NO: 8.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsvaerd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5- fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having endoglucanase activity. In one aspect, a subsequence contains at least 900 nucleotides, e.g., at least 1000 nucleotides or at least 1100 nucleotides of SEQ ID NO: 1, SEQ ID NO: 3, SEQ ID NO: 5, or SEQ ID NO: 7.

Variant: The term "variant" means a polypeptide having endoglucanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

Polypeptides Having Endoglucanase Activity

In an embodiment, the present invention relates to isolated polypeptides having a sequence identity to the mature polypeptide of SEQ ID NO: 2 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have endoglucanase activity. In an embodiment, the present invention relates to isolated polypeptides having a sequence identity to the mature polypeptide of SEQ ID NO: 4 of at least 71%, e.g., at least 72%, at least 73%, at least 74%, at least 75%, at least 76%, at least 77%, at least 78%, at least 79%, at least 80%, at least 81%, at least 83%, at least 85%, at least 87%, at least 90%, at least 91%, at least 92%, at least 93%, at least 94%, at least 95%, at least 96%, at least 97%, at least 98%, at least 99%, or 100%, which have endoglucanase activity. In an embodiment, the present invention relates to isolated polypeptides having a sequence identity to the mature polypeptide of SEQ ID NO: 6 of at least 74%, e.g., at least 75%, at least 76%, at least 77%, at least 78%, at least 79%, at least 80%, at least 81%, at least 82%, at least 83%, at least 85%, at least 87%, at least 90%, at least 91%, at least 92%, at least 93%, at least 94%, at least 95%, at least 96%, at least 97%, at least 98%, at least 99%, or 100%, which have endoglucanase activity. In an embodiment, the present invention relates to isolated polypeptides having a sequence identity to the mature polypeptide of SEQ ID NO: 8 of at least 75%, e.g., at least 76%, at least 77%, at least 78%, at least 79%, at least 80%, at least 81%, at least 82%, at least 83%, at least 85%, at least 87%, at least 90%, at least 91%, at least 92%, at least 93%, at least 94%, at least 95%, at least 96%, at least 97%, at least 98%, at least 99%, or 100%, which have endoglucanase activity. In one aspect, the polypeptides differ by no more than 10 amino acids, e.g., 1, 2, 3, 4, 5, 6, 7, 8, or 9, from the mature polypeptide of SEQ ID NO: 2, SEQ ID NO: 4, SEQ ID NO: 6, or SEQ ID NO: 8.

A polypeptide of the present invention preferably comprises or consists of the amino acid sequence of SEQ ID NO: 2, SEQ ID NO: 4, SEQ ID NO: 6, or SEQ ID NO: 8 or an allelic variant thereof; or is a fragment thereof having endoglucanase activity. In another aspect, the polypeptide comprises or consists of the mature polypeptide of SEQ ID NO: 2, SEQ ID NO: 4, SEQ ID NO: 6, or SEQ ID NO: 8. In another aspect, the polypeptide comprises or consists of amino acids 23 to 348 of SEQ ID NO: 2, amino acids 24 to 402 of SEQ ID NO: 4, amino acids 21 to 420 of SEQ ID NO: 6, or amino acids 20 to 396 of SEQ ID NO: 8.

In another embodiment, the present invention relates to an isolated polypeptide having endoglucanase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, SEQ ID NO: 3, SEQ ID NO: 5, or SEQ ID NO: 7, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 1, SEQ ID NO: 3, SEQ ID NO: 5, or SEQ ID NO: 7, or a subsequence thereof, as well as the polypeptide of SEQ ID NO: 2, SEQ ID NO: 4, SEQ ID NO: 6, or SEQ ID NO: 8, or a fragment thereof, may be used to design nucleic acid probes to identify and clone DNA encoding polypeptides having endoglucanase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having endoglucanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 5, or SEQ ID NO: 7 or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 3, SEQ ID NO: 5, or SEQ ID NO: 7; (ii) the mature polypeptide coding sequence of SEQ ID NO: 1, SEQ ID NO: 3, SEQ ID NO: 5, or SEQ ID NO: 7; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, SEQ ID NO: 4, SEQ ID NO: 6, or SEQ ID NO: 8; the mature polypeptide thereof; or a fragment thereof. In another aspect, the nucleic acid probe is SEQ ID NO: 1, SEQ ID NO: 3, SEQ ID NO: 5, or SEQ ID NO: 7; or the cDNA sequence thereof.

In another embodiment, the present invention relates to an isolated polypeptide having endoglucanase activity encoded by a polynucleotide having a sequence identity to the mature polypeptide coding sequence of SEQ ID NO: 1, SEQ ID NO: 3, SEQ ID NO: 5, or SEQ ID NO: 7, or the cDNA sequence thereof, of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, SEQ ID NO: 6, or SEQ ID NO: 8 comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, SEQ ID NO: 6, or SEQ ID NO: 8 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for endoglucanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No.

5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Endoglucanase Activity

A polypeptide having endoglucanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a *Hohenbuehelia* polypeptide.

In another aspect, the polypeptide is a *Hohenbuehelia mastrucata* polypeptide, e.g., a polypeptide obtained from *Hohenbuehelia mastrucata* Strain NN009379.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

The present invention also relates to isolated polypeptides comprising a catalytic domain selected from the group consisting of:

(a) a catalytic domain having at least 60% sequence identity to the catalytic domain of SEQ ID NO: 2 (for example, amino acids 37 to 348 of SEQ ID NO: 2), SEQ ID NO: 4 (for example, amino acids 90 to 402 of SEQ ID NO: 4), SEQ ID NO: 6 (for example, amino acids 94 to 420 of SEQ ID NO: 6), or SEQ ID NO: 8 (for example, amino acids 84 to 396 of SEQ ID NO: 8);

(b) a catalytic domain encoded by a polynucleotide having at least 60% sequence identity to the catalytic domain coding sequence of SEQ ID NO: 1 (for example, nucleotides 106-231, 288-407, 466-511, 564-612, 672-682, 741-766, 824-848, 905-954, 1007-1070, 1127-1150, 1211-1279, 1336-1488, 1544-1644, and 1700-1774 of SEQ ID NO: 1), SEQ ID NO: 3 (for example, nucleotides 381-503, 559-678, 734-779, 838-886, 940-950, 1010-1035, 1095-1119, 1179-1228, 1288-1351, 1410-1433, 1489-1557, 1624-1776, 1845-1948, and 2022-2096 of SEQ ID NO: 3), SEQ ID NO: 5 (for example, nucleotides 453-558, 608-759, 811-876, 927-1024, 1077-1160, 1212-1549, and 1600-1736 of SEQ ID NO: 5), or SEQ ID NO: 7 (for example, nucleotides 485-532, 592-685, 747-752, 804-925, 977-1093, 1143-1263, 1317-1418, 1471-1523, 1573-1682, 1740-1888, and 1941-1957 of SEQ ID NO: 7);

(c) a variant of a catalytic domain comprising a substitution, deletion, and/or insertion of one or more (several) amino acids of the catalytic domain of SEQ ID NO: 2, SEQ ID NO: 4, SEQ ID NO: 6, or SEQ ID NO: 8; and (d) a fragment of a catalytic domain of (a), (b), or (c), which has endoglucanase activity.

The catalytic domain preferably has a degree of sequence identity to the catalytic domain of SEQ ID NO: 2, SEQ ID NO: 4, SEQ ID NO: 6, or SEQ ID NO: 8 of at least 60%, e.g. at least 70%, at least 75%, at least 80%, at least 85%, at least 90%, at least 91%, at least 92%, at least 95%, at least 96%, at least 97%, at least 98%, at least 99%, or 100%. In an aspect, the catalytic domain comprises an amino acid sequence that differs by ten amino acids, e.g., by five amino acids, by four amino acids, by three amino acids, by two amino acids, and by one amino acid from the catalytic domain of SEQ ID NO: 2, SEQ ID NO: 4, SEQ ID NO: 6, or SEQ ID NO: 8.

The catalytic domain preferably comprises or consists of the catalytic domain of SEQ ID NO: 2 or an allelic variant thereof; or is a fragment thereof having endoglucanase activity. In another preferred aspect, the catalytic domain comprises or consists of amino acids 37 to 348 of SEQ ID NO: 2.

The catalytic domain preferably comprises or consists of the catalytic domain of SEQ ID NO: 4 or an allelic variant thereof; or is a fragment thereof having endoglucanase activity. In another preferred aspect, the catalytic domain comprises or consists of amino acids 90 to 402 of SEQ ID NO: 4.

The catalytic domain preferably comprises or consists of the catalytic domain of SEQ ID NO: 6 or an allelic variant thereof; or is a fragment thereof having endoglucanase activity. In another preferred aspect, the catalytic domain comprises or consists of amino acids 94 to 420 of SEQ ID NO: 6.

The catalytic domain preferably comprises or consists of the catalytic domain of SEQ ID NO: 8 or an allelic variant thereof; or is a fragment thereof having endoglucanase activity. In another preferred aspect, the catalytic domain comprises or consists of amino acids 84 to 396 of SEQ ID NO: 8.

In an embodiment, the catalytic domain may be encoded by a polynucleotide that hybridizes under very low stringency conditions, low stringency conditions, medium stringency conditions, medium-high stringency conditions, high stringency conditions, and very high stringency conditions (as defined above) with (i) the catalytic domain coding sequence of SEQ ID NO: 1, SEQ ID NO: 3, SEQ ID NO: 5, or SEQ ID NO: 7, (ii) the cDNA sequence contained in the catalytic domain coding sequence of SEQ ID NO: 1, SEQ ID NO: 3, SEQ ID NO: 5, or SEQ ID NO: 7, or (iii) the full-length complementary strand of (i) or (ii) (J. Sambrook et al., 1989, supra).

The catalytic domain may be encoded by a polynucleotide having a degree of sequence identity to the catalytic domain coding sequence of SEQ ID NO: 1, SEQ ID NO: 3, SEQ ID NO: 5, or SEQ ID NO: 7 of at least 60%, e.g. at least 70%, at least 75%, at least 80%, at least 85%, at least 90%, at least 91%, at least 92%, at least 95%, at least 96%, at least 97%, at least 98%, at least 99%, or 100%, which encode a polypeptide having endoglucanase activity.

In one aspect, the polynucleotide encoding the catalytic domain comprises or consists of nucleotides 106 to 1774 of SEQ ID NO: 1 or the cDNA sequence thereof. In particular the polynucleotide encoding the catalytic domain comprises or consists of nucleotides 106-231, 288-407, 466-511, 564-612, 672-682, 741-766, 824-848, 905-954, 1007-1070, 1127-1150, 1211-1279, 1336-1488, 1544-1644, and 1700-1774 of SEQ ID NO: 1.

In one aspect, the polynucleotide encoding the catalytic domain comprises or consists of nucleotides 381 to 2096 of SEQ ID NO: 3 or the cDNA sequence thereof. In particular the polynucleotide encoding the catalytic domain comprises or consists of nucleotides 381-503, 559-678, 734-779, 838-886, 940-950, 1010-1035, 1095-1119, 1179-1228, 1288-1351, 1410-1433, 1489-1557, 1624-1776, 1845-1948, and 2022-2096 of SEQ ID NO: 3.

In one aspect, the polynucleotide encoding the catalytic domain comprises or consists of nucleotides 453 to 1736 of SEQ ID NO: 5 or the cDNA sequence thereof. In particular the polynucleotide encoding the catalytic domain comprises or consists of nucleotides 453-558, 608-759, 811-876, 927-1024, 1077-1160, 1212-1549, and 1600-1736 of SEQ ID NO: 5.

In one aspect, the polynucleotide encoding the catalytic domain comprises or consists of nucleotides 485 to 1957 of SEQ ID NO: 7 or the cDNA sequence thereof. In particular the polynucleotide encoding the catalytic domain comprises or consists of nucleotides 485-532, 592-685, 747-752, 804-925, 977-1093, 1143-1263, 1317-1418, 1471-1523, 1573-1682, 1740-1888, and 1941-1957 of SEQ ID NO: 7.

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Hohenbuehelia*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, SEQ ID NO: 5, or SEQ ID NO: 7, or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus neutral* alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* ctyIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase,

*Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a *Hohenbuehelia* cell. In a more preferred aspect, the cell is a *Hohenbuehelia mastrucata* cell. In a most preferred aspect, the cell is *Hohenbuehelia mastrucata* Strain NN009379.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium,* temperate grass, such as *Agrostis,* and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Compositions

The present invention also relates to compositions comprising a polypeptide of the present invention. Preferably, the compositions are enriched in such a polypeptide. The term "enriched" indicates that the endoglucanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as one or more (e.g., several) enzymes selected from the group consisting of a cellulase, a hemicellulase, GH61 polypeptide, an expansin, an esterase, a laccase, a ligninolytic enzyme, a pectinase, a peroxidase, a protease, and a swollen in.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to the following processes for using the polypeptides having endoglucanase activity, or compositions thereof.

The present invention also relates to processes for degrading a cellulosic material, comprising: treating the cellulosic material with an enzyme composition in the presence of a polypeptide having endoglucanase activity of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a polypeptide having endoglucanase activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having endoglucanase activity of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment:

The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a polypeptide having endoglucanase activity of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin In the processes of the present invention, the enzyme(s) can be added prior to or during fermentation, e.g., during saccharification or during or after propagation of the fermenting microorganism(s).

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a crude fermentation broth with or without cells removed, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having endoglucanase activity depend on several factors including, but not limited to, the mixture of component cellulolytic enzymes, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a polypeptide having endoglucanase activity to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a polypeptide having endoglucanase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, *Caldicellulosiruptor*, *Acidothermus*, *Thermobifidia*, or *Oceanobacillus* polypeptide having enzyme activity, or a Gram negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* polypeptide having enzyme activity.

In one aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having enzyme activity.

In another aspect, the polypeptide is a *Streptococcus equisimilis*, *Streptococcus pyogenes*, *Streptococcus uberis*, or *Streptococcus* equi subsp. *Zooepidemicus* polypeptide having enzyme activity.

In another aspect, the polypeptide is a *Streptomyces achromogenes*, *Streptomyces avermitilis*, *Streptomyces coelicolor*, *Streptomyces griseus*, or *Streptomyces lividans* polypeptide having enzyme activity.

The polypeptide having enzyme activity may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having enzyme activity; or more preferably a filamentous fungal polypeptide such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide having enzyme activity.

In one aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having enzyme activity.

In another aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia spededonium*, *Thielavia setosa*, *Thielavia subthermophila*, *Thielavia terrestris*, *Trichoderma harzianum*, *Trichoderma koningii*, *Trichoderma longibrachiatum*, *Trichoderma reesei*, *Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC™ CTec (Novozymes A/S), CELLIC™ CTec2 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM). ROHAMENT™ 7069 W (Röhm GmbH), FIBREZYME® LDI (Dyadic International, Inc.), FIBREZYME® LBR (Dyadic International, Inc.), or VISCOSTAR® 150 L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, Gene 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydralase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In the processes of the present invention, any GH61 polypeptide having cellulolytic enhancing activity can be used.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus sp.* (WO 2011/039319), *Penicillium sp.* (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese sulfate.

In one aspect, the GH61 polypeptide having cellulolytic enhancing activity is used in the presence of a dioxy compound, a bicyclic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzoxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 μM to about 10 mM, about 5 μM to about 5 mM, ord about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC™ HTec (Novozymes A/S), CELLIC™ HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8×212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8X211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is (are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae*; *Clostridium*, such as *C. acetobutylicum, C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus, K. lactis, K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacilus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol*. 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to an isolated polynucleotide encoding a signal peptide comprising or consisting of amino acids 1 to 22 of SEQ ID NO: 2, amino acids 1 to 23 of SEQ ID NO: 4, amino acids 1 to 20 of SEQ ID NO: 6, or amino acids 1 to 19 of SEQ ID NO: 8. The polynucleotide may further comprise a gene encoding a protein, which is operably linked to the signal peptide. The protein is preferably foreign to the signal peptide. In one aspect, the polynucleotide encoding the signal peptide is nucleotides 1 to 63 of SEQ ID NO: 1. In another aspect, the polynucleotide encoding the signal peptide is nucleotides 1 to 69 of SEQ ID NO: 3. In another aspect, the polynucleotide encoding the signal peptide is nucleotides 1 to 60 of SEQ ID NO: 5. In another aspect, the polynucleotide encoding the signal peptide is nucleotides 1 to 57 of SEQ ID NO: 7.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A nucleic acid construct comprising a polynucleotide encoding a polypeptide having endoglucanase activity, wherein the polynucleotide is operably linked to one or more heteroloqous control sequences that direct the production of the polypeptide in an expression host, and wherein the polypeptide having endoglucanase activity comprises:
   an amino acid sequence having at least 95% sequence identity to the mature polypeptide of SEQ ID NO: 2, at least 95% sequence identity to the mature polypeptide of SEQ ID NO: 4, at least 95% sequence identity to the mature polypeptide of SEQ ID NO: 6, or at least 95% sequence identity to the mature polypeptide of SEQ ID NO: 8.

2. A process for degrading a cellulosic material, said process comprising:
   (i) treating the cellulosic material with an enzyme composition, wherein the composition comprises a polypeptide having endoglucanase activity; and
   (ii) recovering the degraded material;
   wherein the polypeptide having endoglucanase activity comprises at least 95% sequence identity to the mature polypeptide of SEQ ID NO: 2, at least 95% sequence identity to the mature polypeptide of SEQ ID NO: 4, at least 95% sequence identity to the mature polypeptide of SEQ ID NO: 6, or at least 95% sequence identity to the mature polypeptide of SEQ ID NO: 8.

3. A process for producing a fermentation product, said process comprising:
   (a) saccharifying a cellulosic material with an enzyme composition, wherein the composition comprises a polypeptide having endoglucanase activity;
   (b) fermenting the saccharified cellulosic material with one or more fermenting microorganisms to produce the fermentation product; and
   (c) recovering the fermentation product from the fermentation;
   wherein the polypeptide having endoglucanase activity comprises at least 95% sequence identity to the mature polypeptide of SEQ ID NO: 2, at least 95% sequence identity to the mature polypeptide of SEQ ID NO: 4, at least 95% sequence identity to the mature polypeptide of SEQ ID NO: 6, or at least 95% sequence identity to the mature polypeptide of SEQ ID NO: 8.

4. A recombinant expression vector comprising the nucleic acid construct of claim 1.

5. A recombinant host cell comprising the nucleic acid construct of claim 1.

6. A method of producing a polypeptide having endoglucanase activity, comprising:
   (a) cultivating the host cell of claim 5 under conditions conducive for production of the polypeptide; and
   (b) recovering the polypeptide.

7. A transgenic plant, plant part or plant cell transformed with the nucleic acid construct of claim 1.

8. A method of producing a polypeptide having endoglucanase activity, comprising:
   (a) cultivating the transgenic plant or plant cell of claim 7 under conditions conducive for production of the polypeptide; and
   (b) recovering the polypeptide.

9. A nucleic acid construct or expression vector comprising a gene encoding a protein,
   wherein the gene is operably linked to a polynucleotide that encodes a signal peptide comprising or consisting of amino acids 1 to 22 of SEQ ID NO: 2, amino acids 1 to 23 of SEQ ID NO: 4, amino acids 1 to 20 of SEQ ID NO: 6, or amino acids 1 to 19 of SEQ ID NO: 8, and
   wherein the gene is foreign to the polynucleotide encoding the signal peptide.

10. An isolated recombinant host cell comprising the nucleic acid construct or expression vector of claim 9.

11. A method of producing a protein, said method comprising:
    (a) cultivating the recombinant host cell of claim 10 under conditions conducive for production of the protein; and
    (b) recovering the protein.

12. The nucleic acid construct of claim 1, wherein the polypeptide having endoglucanase activity comprises an amino acid sequence having at least 95% sequence identity to mature polypeptide of SEQ ID NO: 2.

13. The nucleic acid construct of claim 1, wherein the polypeptide having endoglucanase activity comprises an amino acid sequence having at least 97% sequence identity to mature polypeptide of SEQ ID NO: 2.

14. The nucleic acid construct of claim 1, wherein the polypeptide having endoglucanase activity comprises an amino acid sequence having at least 98% sequence identity to mature polypeptide of SEQ ID NO: 2.

15. The nucleic acid construct of claim 1, wherein the polypeptide having endoglucanase activity comprises an amino acid sequence having at least 99% sequence identity to mature polypeptide of SEQ ID NO: 2.

16. The nucleic acid construct of claim 1, wherein the polypeptide having endoglucanase activity comprises the amino acid sequence of SEQ ID NO: 2.

17. The nucleic acid construct of claim 1, wherein the polypeptide having endoglucanase activity comprises an amino acid sequence having amino acids 23 to 348 of SEQ ID NO: 2.

18. The nucleic acid construct of claim 1, wherein the polypeptide having endoglucanase activity comprises an amino acid sequence having at least 95% sequence identity to mature polypeptide of SEQ ID NO: 4.

19. The nucleic acid construct of claim 1, wherein the polypeptide having endoglucanase activity comprises an amino acid sequence having at least 97% sequence identity to mature polypeptide of SEQ ID NO: 4.

20. The nucleic acid construct of claim 1, wherein the polypeptide having endoglucanase activity comprises an amino acid sequence having at least 98% sequence identity to mature polypeptide of SEQ ID NO: 4.

21. The nucleic acid construct of claim 1, wherein the polypeptide having endoglucanase activity comprises an amino acid sequence having at least 99% sequence identity to mature polypeptide of SEQ ID NO: 4.

22. The nucleic acid construct of claim 1, wherein the polypeptide having endoglucanase activity comprises the amino acid sequence of SEQ ID NO: 4.

23. The nucleic acid construct of claim 1, wherein the polypeptide having endoglucanase activity comprises an amino acid sequence having amino acids 24 to 402 of SEQ ID NO: 4.

24. The nucleic acid construct of claim 1, wherein the polypeptide having endoglucanase activity comprises an amino acid sequence having at least 95% sequence identity to mature polypeptide of SEQ ID NO: 6.

25. The nucleic acid construct of claim 1, wherein the polypeptide having endoglucanase activity comprises an amino acid sequence having at least 97% sequence identity to mature polypeptide of SEQ ID NO: 6.

26. The nucleic acid construct of claim 1, wherein the polypeptide having endoglucanase activity comprises an amino acid sequence having at least 98% sequence identity to mature polypeptide of SEQ ID NO: 6.

27. The nucleic acid construct of claim 1, wherein the polypeptide having endoglucanase activity comprises an amino acid sequence having at least 99% sequence identity to mature polypeptide of SEQ ID NO: 6.

28. The nucleic acid construct of claim 1, wherein the polypeptide having endoglucanase activity comprises the amino acid sequence of SEQ ID NO: 6.

29. The nucleic acid construct of claim 1, wherein the polypeptide having endoglucanase activity comprises an amino acid sequence having amino acids 21 to 420 of SEQ ID NO: 6.

30. The nucleic acid construct of claim 1, wherein the polypeptide having endoglucanase activity comprises an amino acid sequence having at least 95% sequence identity to mature polypeptide of SEQ ID NO: 8.

31. The nucleic acid construct of claim 1, wherein the polypeptide having endoglucanase activity comprises an amino acid sequence having at least 97% sequence identity to mature polypeptide of SEQ ID NO: 8.

32. The nucleic acid construct of claim 1, wherein the polypeptide having endoglucanase activity comprises an amino acid sequence having at least 98% sequence identity to mature polypeptide of SEQ ID NO: 8.

33. The nucleic acid construct of claim 1, wherein the polypeptide having endoglucanase activity comprises an amino acid sequence having at least 99% sequence identity to mature polypeptide of SEQ ID NO: 8.

34. The nucleic acid construct of claim 1, wherein the polypeptide having endoglucanase activity comprises the amino acid sequence of SEQ ID NO: 8.

35. The nucleic acid construct of claim 1, wherein the polypeptide having endoglucanase activity comprises an amino acid sequence having amino acids 20 to 396 of SEQ ID NO: 8.

36. An isolated recombinant host cell transformed with a polynucleotide encoding a polypeptide having endoglucanase activity, wherein the polynucleotide is heterologous to the recombinant host cell, and wherein the polypeptide having endoglucanase activity comprises at least 95% sequence identity to the mature polypeptide of SEQ ID NO: 2, at least 95% sequence identity to the mature polypeptide of SEQ ID NO: 4, at least 95% sequence identity to the mature polypeptide of SEQ ID NO: 6, or at least 95% sequence identity to the mature polypeptide of SEQ ID NO: 8.

* * * * *

SEQUENCE LISTING

```
<160> NUMBER OF SEQ ID NOS: 8

<210> SEQ ID NO 1
<211> LENGTH: 1777
<212> TYPE: DNA
<213> ORGANISM: Hohenbuehelia mastrucata
```

```
<220> FEATURE:
<221> NAME/KEY: CDS
<222> LOCATION: (1)..(231)
<220> FEATURE:
<221> NAME/KEY: sig_peptide
<222> LOCATION: (1)..(63)
<220> FEATURE:
<221> NAME/KEY: mat_peptide
<222> LOCATION: (64)..()
<220> FEATURE:
<221> NAME/KEY: Intron
<222> LOCATION: (232)..(287)
<220> FEATURE:
<221> NAME/KEY: CDS
<222> LOCATION: (288)..(407)
<220> FEATURE:
<221> NAME/KEY: Intron
<222> LOCATION: (408)..(465)
<220> FEATURE:
<221> NAME/KEY: CDS
<222> LOCATION: (466)..(511)
<220> FEATURE:
<221> NAME/KEY: Intron
<222> LOCATION: (512)..(563)
<220> FEATURE:
<221> NAME/KEY: CDS
<222> LOCATION: (564)..(612)
<220> FEATURE:
<221> NAME/KEY: Intron
<222> LOCATION: (613)..(671)
<220> FEATURE:
<221> NAME/KEY: CDS
<222> LOCATION: (672)..(682)
<220> FEATURE:
<221> NAME/KEY: Intron
<222> LOCATION: (683)..(740)
<220> FEATURE:
<221> NAME/KEY: CDS
<222> LOCATION: (741)..(766)
<220> FEATURE:
<221> NAME/KEY: Intron
<222> LOCATION: (767)..(823)
<220> FEATURE:
<221> NAME/KEY: CDS
<222> LOCATION: (824)..(848)
<220> FEATURE:
<221> NAME/KEY: Intron
<222> LOCATION: (849)..(904)
<220> FEATURE:
<221> NAME/KEY: CDS
<222> LOCATION: (905)..(954)
<220> FEATURE:
<221> NAME/KEY: Intron
<222> LOCATION: (955)..(1006)
<220> FEATURE:
<221> NAME/KEY: CDS
<222> LOCATION: (1007)..(1070)
<220> FEATURE:
<221> NAME/KEY: Intron
<222> LOCATION: (1071)..(1126)
<220> FEATURE:
<221> NAME/KEY: CDS
<222> LOCATION: (1127)..(1150)
<220> FEATURE:
<221> NAME/KEY: Intron
<222> LOCATION: (1151)..(1210)
<220> FEATURE:
<221> NAME/KEY: CDS
<222> LOCATION: (1211)..(1279)
<220> FEATURE:
<221> NAME/KEY: Intron
<222> LOCATION: (1280)..(1335)
<220> FEATURE:
<221> NAME/KEY: CDS
<222> LOCATION: (1336)..(1488)
<220> FEATURE:
<221> NAME/KEY: Intron
<222> LOCATION: (1489)..(1543)
<220> FEATURE:
```

```
<221> NAME/KEY: CDS
<222> LOCATION: (1544)..(1644)
<220> FEATURE:
<221> NAME/KEY: Intron
<222> LOCATION: (1645)..(1699)
<220> FEATURE:
<221> NAME/KEY: CDS
<222> LOCATION: (1700)..(1774)

<400> SEQUENCE: 1
```

| | | | | | | | | | | | | | | | | |
|---|---|---|---|---|---|---|---|---|---|---|---|---|---|---|---|---|
| atg | ctg | tcc | agg | tca | ctc | ttt | gtt | tcg | ttg | gct | ata | ttc | gct | tcg | gtg | 48 |
| Met | Leu | Ser | Arg | Ser | Leu | Phe | Val | Ser | Leu | Ala | Ile | Phe | Ala | Ser | Val | |
| | -20 | | | | -15 | | | | | -10 | | | | | | |

| | | | | | | | | | | | | | | | | |
|---|---|---|---|---|---|---|---|---|---|---|---|---|---|---|---|---|
| gct | aca | ccc | gct | gct | gcg | gct | gtt | ctg | cca | cct | acc | tcc | acc | aca | act | 96 |
| Ala | Thr | Pro | Ala | Ala | Ala | Ala | Val | Leu | Pro | Pro | Thr | Ser | Thr | Thr | Thr | |
| -5 | | | | -1 | 1 | | | | 5 | | | | | 10 | | |

| | | | | | | | | | | | | | | | | |
|---|---|---|---|---|---|---|---|---|---|---|---|---|---|---|---|---|
| gcc | gca | gat | gcc | tgc | ccc | aac | gcc | acg | aaa | ttc | aag | ttc | ttt | ggc | gtc | 144 |
| Ala | Ala | Asp | Ala | Cys | Pro | Asn | Ala | Thr | Lys | Phe | Lys | Phe | Phe | Gly | Val | |
| | | 15 | | | | | 20 | | | | | 25 | | | | |

| | | | | | | | | | | | | | | | | |
|---|---|---|---|---|---|---|---|---|---|---|---|---|---|---|---|---|
| aac | gaa | tct | ggc | gcc | gaa | ttt | ggc | aac | caa | aac | att | cct | ggt | gtg | ctt | 192 |
| Asn | Glu | Ser | Gly | Ala | Glu | Phe | Gly | Asn | Gln | Asn | Ile | Pro | Gly | Val | Leu | |
| | 30 | | | | | 35 | | | | | 40 | | | | | |

| | | | | | | | | | | | |
|---|---|---|---|---|---|---|---|---|---|---|---|
| gga | aca | gac | tac | acc | tgg | cca | tcg | ccg | tcc | tct | atc gac gtatgtatca | 241 |
| Gly | Thr | Asp | Tyr | Thr | Trp | Pro | Ser | Pro | Ser | Ser | Ile Asp | |
| | 45 | | | | | 50 | | | | | 55 | |

| | | | | |
|---|---|---|---|---|
| aaagtgacga cacgatggac agtaatctga tgtttctggg cgttag ttc ttc acc | 296 |
| Phe Phe Thr | |

| | | | | | | | | | | | | | | | | |
|---|---|---|---|---|---|---|---|---|---|---|---|---|---|---|---|---|
| gac | aaa | ggc | ttc | aac | gcc | ttc | cgc | att | cct | ttc | cag | ctt | gag | cgt | ctc | 344 |
| Asp | Lys | Gly | Phe | Asn | Ala | Phe | Arg | Ile | Pro | Phe | Gln | Leu | Glu | Arg | Leu | |
| 60 | | | | | 65 | | | | | 70 | | | | | 75 | |

| | | | | | | | | | | | | | | | | |
|---|---|---|---|---|---|---|---|---|---|---|---|---|---|---|---|---|
| agt | ccg | cca | gcg | act | ggt | ctc | aca | ggc | gca | ttc | gat | gcg | aca | tac | cta | 392 |
| Ser | Pro | Pro | Ala | Thr | Gly | Leu | Thr | Gly | Ala | Phe | Asp | Ala | Thr | Tyr | Leu | |
| | | | | 80 | | | | | 85 | | | | | 90 | | |

| | | | | | | |
|---|---|---|---|---|---|---|
| agt | ggt | ctc | caa | acg | gtgggtaacc tattatttac gatcctaact ctggagcatg | 447 |
| Ser | Gly | Leu | Gln | Thr | | |
| | | | 95 | | | |

| | | | | | | | | | | | |
|---|---|---|---|---|---|---|---|---|---|---|---|
| acagattcca ttcactag | att | gtt | gaa | tac | atc | acg | agc | aaa | ggc | gca | ttt | 498 |
| | Ile | Val | Glu | Tyr | Ile | Thr | Ser | Lys | Gly | Ala | Phe | |
| | | | | 100 | | | | | 105 | | | |

| | | | | |
|---|---|---|---|---|
| gct | gct | atc | gag c gtaggtttcc tttaccgcta ccaaagtgta ttcaactaaa | 551 |
| Ala | Ala | Ile | Glu | |
| | | 110 | | |

| | | | | | | | | |
|---|---|---|---|---|---|---|---|---|
| ccctaatgat ag cc | cac | aac | ttt | atg | atc | tac | aat ggc gcc caa att act | 601 |
| | Pro | His | Asn | Phe | Met | Ile | Tyr Asn Gly Ala Gln Ile Thr | |
| | | | | 115 | | | 120 | |

| | | | | |
|---|---|---|---|---|
| tct | acc | gcg | ga gtaagtggga atacattatt tccttgtctt tactgacgct | 652 |
| Ser | Thr | Ala | Asp | |
| 125 | | | | |

| | | | | | |
|---|---|---|---|---|---|
| tttgattttg cgcaaatag t | ttc | gcc | aca | t gttcgtattc aacctaagtc | 702 |
| | Phe | Ala | Thr | | |
| | | 130 | | | |

| | | | | | | |
|---|---|---|---|---|---|---|
| tatctcagat tgaattattt gctcattcac aagcacag tc | tgg | cag | aac | cta | gcc | 757 |
| | Phe Trp | Gln | Asn | Leu | Ala | |
| | | | | | 135 | |

| | | | | |
|---|---|---|---|---|
| acg | atc | ttc | gtacgtcatg tcatgctcgc ccgtgtcacc ctaccagta | 806 |
| Thr | Ile | Phe | | |
| | | 140 | | |

| | | | | | | | | |
|---|---|---|---|---|---|---|---|---|
| ctcaggtcat gcttcag | aaa | gat | aac | gca | aac | gtc | att | ttc g gtatgaacag | 858 |
| | Lys | Asp | Asn | Ala | Asn | Val | Ile | Phe | |
| | | | | 145 | | | | |

| | | | |
|---|---|---|---|
| ggcagagacc cgactggcat aagatgacaa tctccgcatt tttcag | at | ata | atc | 912 |
| | | | |

```
                                        Asp Ile Ile
                                                150 aac gag cct cat gac atg cct gcc act act gtg ttc gat ctg         954
Asn Glu Pro His Asp Met Pro Ala Thr Thr Val Phe Asp Leu
        155                 160                 165 gtacgccctt tgtatccgcg caaaacagga cattcctcgt tcatgattat ag aat caa   1012
                                                          Asn Gln gcc gcg gtg aat ggt atc cgc gcc agc gga gct acg tca cag ttg ata   1060
Ala Ala Val Asn Gly Ile Arg Ala Ser Gly Ala Thr Ser Gln Leu Ile
        170                 175                 180 ctc gtc gag g gtatgctgtt cttgcggtca tctacatgta atggatctaa          1110
Leu Val Glu
    185 cacagcggtt atcaag ga  aca tcc tgg act ggc gcg tgg a gtaggtcaca    1160
                     Gly Thr Ser Trp Thr Gly Ala Trp
                              190 gctcacaacc atgtcacaat atcgggtccg ctgaaaattt ctctgctcag ca  tgg    1215
                                                           Thr Trp
                                                               195 atc act tcc ggc aac ggc gat gcc ttc gtg ggc att tct gat cct aac   1263
Ile Thr Ser Gly Asn Gly Asp Ala Phe Val Gly Ile Ser Asp Pro Asn
        200                 205                 210 gat aac att gcc att g gtgggatcct tattggttca gctcgaacgc atcaaagctc 1319
Asp Asn Ile Ala Ile
        215 aactccggtt tcgtag ag  atg cac caa tac ctc gac tct gat ggc tct ggg 1370
                     Glu Met His Gln Tyr Leu Asp Ser Asp Gly Ser Gly
                              220                 225 aca tcc gag att tgt gtt tcg cct acc atc ggt gcc gag cga ctc caa   1418
Thr Ser Glu Ile Cys Val Ser Pro Thr Ile Gly Ala Glu Arg Leu Gln
230                 235                 240                 245 gct gcc acg gac tgg ctc aag gcc aat aac ctg aaa ggt ttc ctt ggc   1466
Ala Ala Thr Asp Trp Leu Lys Ala Asn Asn Leu Lys Gly Phe Leu Gly
        250                 255                 260 gag att ggc gcg gga tca aat g gtatgaggtc catcttcttt aatagcccga   1518
Glu Ile Gly Ala Gly Ser Asn
        265 cttactaagc tacctattct gccag cc  gac tgt atc agt gct gtc act ggc   1569
                              Ala Asp Cys Ile Ser Ala Val Thr Gly
                                      270                 275 gcg ttc tgc gct atg cag cag tct gga gtg tgg atc ggc gct ctg tgg   1617
Ala Phe Cys Ala Met Gln Gln Ser Gly Val Trp Ile Gly Ala Leu Trp
        280                 285                 290 tgg gct gct ggg cct tgg tgg ggt gac gtcagtgcat aatcaagcct         1664
Trp Ala Ala Gly Pro Trp Trp Gly Asp
        295                 300 tgcatgactt gtgatgctga tcttcttgtc tttag tac tac cag tct atc gag    1717
                                      Tyr Tyr Gln Ser Ile Glu
                                                          305 cct ccc aat gga cct gcc ctc gcc gag att ctc cct caa gct ctc gag   1765
Pro Pro Asn Gly Pro Ala Leu Ala Glu Ile Leu Pro Gln Ala Leu Glu
        310                 315                 320 cct ttc ctt taa                                                   1777
Pro Phe Leu
325

<210> SEQ ID NO 2
<211> LENGTH: 348
<212> TYPE: PRT
<213> ORGANISM: Hohenbuehelia mastrucata
```

<400> SEQUENCE: 2

```
Met Leu Ser Arg Ser Leu Phe Val Ser Leu Ala Ile Phe Ala Ser Val
    -20                 -15                 -10
Ala Thr Pro Ala Ala Ala Val Leu Pro Pro Thr Ser Thr Thr Thr
-5              -1   1               5                   10
Ala Ala Asp Ala Cys Pro Asn Ala Thr Lys Phe Lys Phe Phe Gly Val
            15                  20                  25
Asn Glu Ser Gly Ala Glu Phe Gly Asn Gln Asn Ile Pro Gly Val Leu
            30                  35                  40
Gly Thr Asp Tyr Thr Trp Pro Ser Pro Ser Ser Ile Asp Phe Phe Thr
            45                  50                  55
Asp Lys Gly Phe Asn Ala Phe Arg Ile Pro Phe Gln Leu Glu Arg Leu
60              65                  70                  75
Ser Pro Pro Ala Thr Gly Leu Thr Gly Ala Phe Asp Ala Thr Tyr Leu
                80                  85                  90
Ser Gly Leu Gln Thr Ile Val Glu Tyr Ile Thr Ser Lys Gly Ala Phe
            95                  100                 105
Ala Ala Ile Glu Pro His Asn Phe Met Ile Tyr Asn Gly Ala Gln Ile
            110                 115                 120
Thr Ser Thr Ala Asp Phe Ala Thr Phe Trp Gln Asn Leu Ala Thr Ile
            125                 130                 135
Phe Lys Asp Asn Ala Asn Val Ile Phe Asp Ile Ile Asn Glu Pro His
140             145                 150                 155
Asp Met Pro Ala Thr Thr Val Phe Asp Leu Asn Gln Ala Ala Val Asn
                160                 165                 170
Gly Ile Arg Ala Ser Gly Ala Thr Ser Gln Leu Ile Leu Val Glu Gly
            175                 180                 185
Thr Ser Trp Thr Gly Ala Trp Thr Trp Ile Thr Ser Gly Asn Gly Asp
            190                 195                 200
Ala Phe Val Gly Ile Ser Asp Pro Asn Asp Asn Ile Ala Ile Glu Met
            205                 210                 215
His Gln Tyr Leu Asp Ser Asp Gly Ser Gly Thr Ser Glu Ile Cys Val
220             225                 230                 235
Ser Pro Thr Ile Gly Ala Glu Arg Leu Gln Ala Ala Thr Asp Trp Leu
                240                 245                 250
Lys Ala Asn Asn Leu Lys Gly Phe Leu Gly Glu Ile Gly Ala Gly Ser
            255                 260                 265
Asn Ala Asp Cys Ile Ser Ala Val Thr Gly Ala Phe Cys Ala Met Gln
            270                 275                 280
Gln Ser Gly Val Trp Ile Gly Ala Leu Trp Trp Ala Ala Gly Pro Trp
            285                 290                 295
Trp Gly Asp Tyr Tyr Gln Ser Ile Glu Pro Pro Asn Gly Pro Ala Leu
300             305                 310                 315
Ala Glu Ile Leu Pro Gln Ala Leu Glu Pro Phe Leu
            320                 325
```

<210> SEQ ID NO 3
<211> LENGTH: 2099
<212> TYPE: DNA
<213> ORGANISM: Hohenbuehelia mastrucata
<220> FEATURE:
<221> NAME/KEY: CDS
<222> LOCATION: (1)..(93)
<220> FEATURE:
<221> NAME/KEY: sig_peptide

```
<222> LOCATION: (1)..(69)
<220> FEATURE:
<221> NAME/KEY: mat_peptide
<222> LOCATION: (70)..()
<220> FEATURE:
<221> NAME/KEY: Intron
<222> LOCATION: (94)..(153)
<220> FEATURE:
<221> NAME/KEY: CDS
<222> LOCATION: (154)..(217)
<220> FEATURE:
<221> NAME/KEY: Intron
<222> LOCATION: (218)..(270)
<220> FEATURE:
<221> NAME/KEY: CDS
<222> LOCATION: (271)..(503)
<220> FEATURE:
<221> NAME/KEY: Intron
<222> LOCATION: (504)..(558)
<220> FEATURE:
<221> NAME/KEY: CDS
<222> LOCATION: (559)..(678)
<220> FEATURE:
<221> NAME/KEY: Intron
<222> LOCATION: (679)..(733)
<220> FEATURE:
<221> NAME/KEY: CDS
<222> LOCATION: (734)..(779)
<220> FEATURE:
<221> NAME/KEY: Intron
<222> LOCATION: (780)..(837)
<220> FEATURE:
<221> NAME/KEY: CDS
<222> LOCATION: (838)..(886)
<220> FEATURE:
<221> NAME/KEY: Intron
<222> LOCATION: (887)..(939)
<220> FEATURE:
<221> NAME/KEY: CDS
<222> LOCATION: (940)..(950)
<220> FEATURE:
<221> NAME/KEY: Intron
<222> LOCATION: (951)..(1009)
<220> FEATURE:
<221> NAME/KEY: CDS
<222> LOCATION: (1010)..(1035)
<220> FEATURE:
<221> NAME/KEY: Intron
<222> LOCATION: (1036)..(1094)
<220> FEATURE:
<221> NAME/KEY: CDS
<222> LOCATION: (1095)..(1119)
<220> FEATURE:
<221> NAME/KEY: Intron
<222> LOCATION: (1120)..(1178)
<220> FEATURE:
<221> NAME/KEY: CDS
<222> LOCATION: (1179)..(1228)
<220> FEATURE:
<221> NAME/KEY: Intron
<222> LOCATION: (1229)..(1287)
<220> FEATURE:
<221> NAME/KEY: CDS
<222> LOCATION: (1288)..(1351)
<220> FEATURE:
<221> NAME/KEY: Intron
<222> LOCATION: (1352)..(1409)
<220> FEATURE:
<221> NAME/KEY: CDS
<222> LOCATION: (1410)..(1433)
<220> FEATURE:
<221> NAME/KEY: Intron
<222> LOCATION: (1434)..(1488)
<220> FEATURE:
<221> NAME/KEY: CDS
<222> LOCATION: (1489)..(1557)
<220> FEATURE:
<221> NAME/KEY: Intron
<222> LOCATION: (1558)..(1623)
```

```
<220> FEATURE:
<221> NAME/KEY: CDS
<222> LOCATION: (1624)..(1776)
<220> FEATURE:
<221> NAME/KEY: Intron
<222> LOCATION: (1777)..(1844)
<220> FEATURE:
<221> NAME/KEY: CDS
<222> LOCATION: (1845)..(1948)
<220> FEATURE:
<221> NAME/KEY: Intron
<222> LOCATION: (1949)..(2021)
<220> FEATURE:
<221> NAME/KEY: CDS
<222> LOCATION: (2022)..(2096)

<400> SEQUENCE: 3 atg cgg tcg gca ctc tct gcg ttc gcc tgt ttg gcg gtc ttg aca tcc        48
Met Arg Ser Ala Leu Ser Ala Phe Ala Cys Leu Ala Val Leu Thr Ser
        -20                 -15                 -10 ctc gtc gct ccg gcg act gcg gtg gct gtc tac gga caa tgc ggt            93
Leu Val Ala Pro Ala Thr Ala Val Ala Val Tyr Gly Gln Cys Gly
    -5             -1  1                 5 gtaagtaatc tttcaattta agtcacgcaa ggctttatcg aatgtacttg cattttaag      153 ggc atc ggt tac act ggc tct acc gtc tgc gat gcg ggc tcg tac tgc       201
Gly Ile Gly Tyr Thr Gly Ser Thr Val Cys Asp Ala Gly Ser Tyr Cys
     10                  15                  20 aag tac acc aat gac t gtaagtatcg aatattgtat gcttgggacc gtctctaata    257
Lys Tyr Thr Asn Asp
 25 atctcaccaa aag gg tac tcc caa tgt cta cct gga agc gac cca aat        305
                Trp Tyr Ser Gln Cys Leu Pro Gly Ser Asp Pro Asn
                 30                  35                  40 gca cct acg tca acc tcc gtg cct gct aca tca tcg tcg tcg aca           353
Ala Pro Thr Ser Thr Ser Val Pro Ala Thr Ser Ser Ser Ser Thr
                 45                  50                  55 tct acc gca cct gcc cca agt ggc agc tgc gcc aac agg aca aag ttc      401
Ser Thr Ala Pro Ala Pro Ser Gly Ser Cys Ala Asn Arg Thr Lys Phe
             60                  65                  70 aag tac ttc ggt gtc aac gag tct ggc gcc gag ttc ggc aac cag aat      449
Lys Tyr Phe Gly Val Asn Glu Ser Gly Ala Glu Phe Gly Asn Gln Asn
 75                  80                  85 atc cct ggt gtc ctt ggt acc gac tac aca tgg ccg tcg ccg tcg tcc      497
Ile Pro Gly Val Leu Gly Thr Asp Tyr Thr Trp Pro Ser Pro Ser Ser
 90                  95                 100                 105 atc gac gtgagtgggc tatccatctc atcaatcttc atcggctgac caataccttg      553
Ile Asp ggcag tac ttc gtc ggc aag ggc ttc aac acc ttc cgc att ccc ttc cag    603
      Tyr Phe Val Gly Lys Gly Phe Asn Thr Phe Arg Ile Pro Phe Gln
           110                 115                 120 ctt gag cgt ctc agc ccg cca gcg cag ggc ctt act ggc tcc ttt gac      651
Leu Glu Arg Leu Ser Pro Pro Ala Gln Gly Leu Thr Gly Ser Phe Asp
         125                 130                 135 gca acc tac ttg gct ggt ctg caa act gtgagtttct tgttgacagt            698
Ala Thr Tyr Leu Ala Gly Leu Gln Thr
         140                 145 acctcgagca tcgaagactg aatgcgcgat gccag att gtt aac tac atc aca        751
                                    Ile Val Asn Tyr Ile Thr
                                                150 agc aag gga gcg tat gct gcc att gaa c gtgagcatct cttgctatag         799
Ser Lys Gly Ala Tyr Ala Ala Ile Glu
         155                 160
```

| | |
|---|---|
| ttgtcaaacg cctgtggctc aagacgcact ttgcttag cc cac aac ttc atg agc<br>                                                                  Pro His Asn Phe Met Ser<br>                                                                             165 | 854 |
| tac aac ggt gct cag atc acc tca acg acc aa gtaagtgaac ttttcggtac<br>Tyr Asn Gly Ala Gln Ile Thr Ser Thr Thr Asn<br>170                  175 | 906 |
| acgcagcgac agcatgctta tttacgtata cag c ttt gcg acc t gtgcgtttaa<br>                                                    Phe Ala Thr<br>                                                    180 | 960 |
| acatagttat caggaaagag ttgttcactg gctgacgcgc tgatcacag gg tgg aag<br>                                                                         Trp Trp Lys<br>                                                                               185 | 1017 |
| aac ctt gcc act gtc ttc gtgagtatcg tctttcatta cctggtgtgt<br>Asn Leu Ala Thr Val Phe<br>                190 | 1065 |
| tcgaataagc ttactcacct gtggcgtag aaa agc aac aat aac gtc att ttc g<br>                                            Lys Ser Asn Asn Asn Val Ile Phe<br>                                                                      195 | 1119 |
| gtgagcgatt cgctgcacaa ttttgatgaa tacattctga atgtatttga tgtgtatag | 1178 |
| at att atg aac gag ccc aac ggc atc gct gca agc act gtc ttc agt<br>Asp Ile Met Asn Glu Pro Asn Gly Ile Ala Ala Ser Thr Val Phe Ser<br>200                   205                   210                   215 | 1225 |
| ctc gtgtgtagcg acttccagac ttgagatacg ctataactca ctatcgtcat<br>Leu | 1278 |
| tcattgcag aac caa gct gca gtc aac ggt att cgc gct tct ggt gct acc<br>              Asn Gln Ala Ala Val Asn Gly Ile Arg Ala Ser Gly Ala Thr<br>                    220                   225                   230 | 1329 |
| aca cag ctc atc ctt gta gaa g gtctgttatc cctatcttaa tcgaagagca<br>Thr Gln Leu Ile Leu Val Glu<br>                  235 | 1381 |
| gctctcgctg atgatgcata ctgtatag ga act gcc tgg acc gga gct tgg a<br>                                           Gly Thr Ala Trp Thr Gly Ala Trp<br>                                                      240                   245 | 1433 |
| gtgcgttttg tacacccagg gtccacgtat cctgaactaa tatattcaat tttag gc<br>                                                                                                Ser | 1490 |
| tgg caa tct tct ggc aat gct gcc gcc ttc gtt gcc ctc acg gat ccc<br>Trp Gln Ser Ser Gly Asn Ala Ala Ala Phe Val Ala Leu Thr Asp Pro<br>       250                   255                   260 | 1538 |
| aac aac aac atc gcc atc g gtgcgtcgct ttagcctctg ccttctcgtc<br>Asn Asn Asn Ile Ala Ile<br>              265 | 1587 |
| ctgatctggt tggctgaata ctccctctgc gcgtag aa atg cac cag tac ctc<br>                                                           Glu Met His Gln Tyr Leu<br>                                                                         270 | 1640 |
| gac tcc gac agc tcc ggc aca tcc ccg acc tgt gta tcc tcc acc atc<br>Asp Ser Asp Ser Ser Gly Thr Ser Pro Thr Cys Val Ser Ser Thr Ile<br>275                   280                   285                   290 | 1688 |
| ggc gtc gag cgc atc caa gcc gcc acg gcg tgg ctc caa cag aac aag<br>Gly Val Glu Arg Ile Gln Ala Ala Thr Ala Trp Leu Gln Gln Asn Lys<br>                  295                   300                   305 | 1736 |
| ctc aag ggc ttc ctc ggg gag atg ggc gcg ggc tcg aac a gtgcgtgtgc<br>Leu Lys Gly Phe Leu Gly Glu Met Gly Ala Gly Ser Asn<br>                310                   315 | 1786 |
| tcaccagcat ttttactttt gccaggtttc tcacgtgtgt tcggttcgct tttggcag | 1844 |
| gc gtc tgc atc gat gct atc aag ggc gcg ctc tgc cat atg cag cag<br>Ser Val Cys Ile Asp Ala Ile Lys Gly Ala Leu Cys His Met Gln Gln<br>320                   325                   330                   335 | 1891 |
| gct ggc ggt aca tgg atc ggg ttc ctc tgg tgg gcg gcc ggt ccc tgg | 1939 |

```
Ala Gly Gly Thr Trp Ile Gly Phe Leu Trp Trp Ala Ala Gly Pro Trp
            340                 345                 350 tgg gga act gtgagtgctc tgtggtcttg tccttgtgca gctgcgagga            1988
Trp Gly Thr tggacggtgc taacgcgtgc tctttgatgg cag tac ttc caa tcg atc gag cca   2042
                                    Tyr Phe Gln Ser Ile Glu Pro
                                        355                 360 ccc aat ggt gca tcg atc tcg cag gtc ctc cca cag gct ctc ata ccg    2090
Pro Asn Gly Ala Ser Ile Ser Gln Val Leu Pro Gln Ala Leu Ile Pro
            365                 370                 375 ttc ttg tag                                                        2099
Phe Leu

<210> SEQ ID NO 4
<211> LENGTH: 402
<212> TYPE: PRT
<213> ORGANISM: Hohenbuehelia mastrucata

<400> SEQUENCE: 4

Met Arg Ser Ala Leu Ser Ala Phe Ala Cys Leu Ala Val Leu Thr Ser
            -20                 -15                 -10

Leu Val Ala Pro Ala Thr Ala Val Ala Val Tyr Gly Gln Cys Gly Gly
        -5              -1  1               5

Ile Gly Tyr Thr Gly Ser Thr Val Cys Asp Ala Gly Ser Tyr Cys Lys
10                  15                  20                  25

Tyr Thr Asn Asp Trp Tyr Ser Gln Cys Leu Pro Gly Ser Asp Pro Asn
                30                  35                  40

Ala Pro Thr Ser Thr Ser Val Pro Ala Thr Ser Ser Ser Ser Ser Thr
            45                  50                  55

Ser Thr Ala Pro Ala Pro Ser Gly Ser Cys Ala Asn Arg Thr Lys Phe
            60                  65                  70

Lys Tyr Phe Gly Val Asn Glu Ser Gly Ala Glu Phe Gly Asn Gln Asn
75                  80                  85

Ile Pro Gly Val Leu Gly Thr Asp Tyr Thr Trp Pro Ser Pro Ser Ser
90                  95                  100                 105

Ile Asp Tyr Phe Val Gly Lys Gly Phe Asn Thr Phe Arg Ile Pro Phe
                110                 115                 120

Gln Leu Glu Arg Leu Ser Pro Pro Ala Gln Gly Leu Thr Gly Ser Phe
            125                 130                 135

Asp Ala Thr Tyr Leu Ala Gly Leu Gln Thr Ile Val Asn Tyr Ile Thr
            140                 145                 150

Ser Lys Gly Ala Tyr Ala Ala Ile Glu Pro His Asn Phe Met Ser Tyr
        155                 160                 165

Asn Gly Ala Gln Ile Thr Ser Thr Thr Asn Phe Ala Thr Trp Trp Lys
170                 175                 180                 185

Asn Leu Ala Thr Val Phe Lys Ser Asn Asn Val Ile Phe Asp Ile
                190                 195                 200

Met Asn Glu Pro Asn Gly Ile Ala Ala Ser Thr Val Phe Ser Leu Asn
            205                 210                 215

Gln Ala Ala Val Asn Gly Ile Arg Ala Ser Gly Ala Thr Thr Gln Leu
            220                 225                 230

Ile Leu Val Glu Gly Thr Ala Trp Thr Gly Ala Trp Ser Trp Gln Ser
        235                 240                 245

Ser Gly Asn Ala Ala Ala Phe Val Ala Leu Thr Asp Pro Asn Asn Asn
250                 255                 260                 265
```

```
Ile Ala Ile Glu Met His Gln Tyr Leu Asp Ser Asp Ser Ser Gly Thr
            270                 275                 280

Ser Pro Thr Cys Val Ser Ser Thr Ile Gly Val Glu Arg Ile Gln Ala
        285                 290                 295

Ala Thr Ala Trp Leu Gln Gln Asn Lys Leu Lys Gly Phe Leu Gly Glu
            300                 305                 310

Met Gly Ala Gly Ser Asn Ser Val Cys Ile Asp Ala Ile Lys Gly Ala
        315                 320                 325

Leu Cys His Met Gln Gln Ala Gly Gly Thr Trp Ile Gly Phe Leu Trp
330                 335                 340                 345

Trp Ala Ala Gly Pro Trp Trp Gly Thr Tyr Phe Gln Ser Ile Glu Pro
                350                 355                 360

Pro Asn Gly Ala Ser Ile Ser Gln Val Leu Pro Gln Ala Leu Ile Pro
            365                 370                 375

Phe Leu

<210> SEQ ID NO 5
<211> LENGTH: 1739
<212> TYPE: DNA
<213> ORGANISM: Hohenbuehelia mastrucata
<220> FEATURE:
<221> NAME/KEY: CDS
<222> LOCATION: (1)..(76)
<220> FEATURE:
<221> NAME/KEY: sig_peptide
<222> LOCATION: (1)..(60)
<220> FEATURE:
<221> NAME/KEY: mat_peptide
<222> LOCATION: (61)..()
<220> FEATURE:
<221> NAME/KEY: Intron
<222> LOCATION: (77)..(134)
<220> FEATURE:
<221> NAME/KEY: CDS
<222> LOCATION: (135)..(145)
<220> FEATURE:
<221> NAME/KEY: Intron
<222> LOCATION: (146)..(209)
<220> FEATURE:
<221> NAME/KEY: CDS
<222> LOCATION: (210)..(267)
<220> FEATURE:
<221> NAME/KEY: Intron
<222> LOCATION: (268)..(318)
<220> FEATURE:
<221> NAME/KEY: CDS
<222> LOCATION: (319)..(558)
<220> FEATURE:
<221> NAME/KEY: Intron
<222> LOCATION: (559)..(607)
<220> FEATURE:
<221> NAME/KEY: CDS
<222> LOCATION: (608)..(759)
<220> FEATURE:
<221> NAME/KEY: Intron
<222> LOCATION: (760)..(810)
<220> FEATURE:
<221> NAME/KEY: CDS
<222> LOCATION: (811)..(876)
<220> FEATURE:
<221> NAME/KEY: Intron
<222> LOCATION: (877)..(926)
<220> FEATURE:
<221> NAME/KEY: CDS
<222> LOCATION: (927)..(1024)
<220> FEATURE:
<221> NAME/KEY: Intron
<222> LOCATION: (1025)..(1076)
<220> FEATURE:
<221> NAME/KEY: CDS
<222> LOCATION: (1077)..(1160)
```

```
<220> FEATURE:
<221> NAME/KEY: Intron
<222> LOCATION: (1161)..(1211)
<220> FEATURE:
<221> NAME/KEY: CDS
<222> LOCATION: (1212)..(1549)
<220> FEATURE:
<221> NAME/KEY: Intron
<222> LOCATION: (1550)..(1599)
<220> FEATURE:
<221> NAME/KEY: CDS
<222> LOCATION: (1600)..(1736)

<400> SEQUENCE: 5 atg aag tct cca tac ttt gct att ctc ttg gcc act gcg ctt cgt gtc       48
Met Lys Ser Pro Tyr Phe Ala Ile Leu Leu Ala Thr Ala Leu Arg Val
-20             -15                 -10                 -5 cgc ggt caa ggc gct ttg tac aca caa t gtgcgttccg cttgacgttt          96
Arg Gly Gln Gly Ala Leu Tyr Thr Gln
        -1  1               5 cccaagccaa gcccatttaa catcctggtc cctaacag gt  ggt ggc gtt            145
                                             Cys Gly Gly Val gtaagtcgta ttcgtcctat tatacgccta ccaaatatta gtgaagctga tattcattca    205 atag ggc tgg aca gga gcg aca act tgc gtc gct ggg gct gta tgc tcc     254
     Gly Trp Thr Gly Ala Thr Thr Cys Val Ala Gly Ala Val Cys Ser
     10                  15                  20 aaa ctg aat gac t gtgggttcat ttcgacgata agtatttcgt aaggctgatt        307
Lys Leu Asn Asp
25 gagttaccca g ac tat tcg cag tgc att cca gga gca gcc gcc ccg tct      356
              Tyr Tyr Ser Gln Cys Ile Pro Gly Ala Ala Ala Pro Ser
              30                  35                  40 tca tct gtg tca tct gtg tca tct tcc gct gcg ccg acg aag gtg tca      404
Ser Ser Val Ser Ser Val Ser Ser Ser Ala Ala Pro Thr Lys Val Ser
            45                  50                  55 act tct gtt gcg tcg acc gga aca acc aca ccg ccg cca act gca gga      452
Thr Ser Val Ala Ser Thr Gly Thr Thr Thr Pro Pro Pro Thr Ala Gly
        60                  65                  70 aag ctc cgt ttt act ggc gtc aat att gcc gga ttc gac ttt ggt tgc      500
Lys Leu Arg Phe Thr Gly Val Asn Ile Ala Gly Phe Asp Phe Gly Cys
    75                  80                  85 tct acc gac ggg aca tgc aac gcc agc ggt gcc tac cca cct ctg ctt      548
Ser Thr Asp Gly Thr Cys Asn Ala Ser Gly Ala Tyr Pro Pro Leu Leu
90                  95                  100                 105 gag tat tac g gcaagttacg ggtttcttcc tgctgggaca cttgctgagt            598
Glu Tyr Tyr gtatcttag gc gct gat gga gaa ggc caa atg aag cac ttt gtc aat gat     648
           Gly Ala Asp Gly Glu Gly Gln Met Lys His Phe Val Asn Asp
           110                 115                 120 gat ggt ttt aac act ttc cgc ctg ccc gtc ggc tgg cag ttt ttg aca      696
Asp Gly Phe Asn Thr Phe Arg Leu Pro Val Gly Trp Gln Phe Leu Thr
        125                 130                 135 aac gat gtg ctc acc ggc act atc aac gag gat aac tgg gtc aag tac      744
Asn Asp Val Leu Thr Gly Thr Ile Asn Glu Asp Asn Trp Val Lys Tyr
    140                 145                 150 gat gct ttg gtc caa gtaggtgccg ctcattccat ctgttgtggg ggtttctgac      799
Asp Ala Leu Val Gln
155 cgatttgta g gcc tgt ctt aac acg gga gca tac tgc atc gtt gac gta      849
            Ala Cys Leu Asn Thr Gly Ala Tyr Cys Ile Val Asp Val
            160                 165                 170
```

```
cat aac tat gcg cgg tgg aat acc aag gtccgttcaa ggtggcctat         896
His Asn Tyr Ala Arg Trp Asn Thr Lys
        175                 180 tcttaaagct tggttctgat tgtcgttcag att att gga cag ggc ggc cca agc   950
                                Ile Ile Gly Gln Gly Gly Pro Ser
                                                    185 aac gag ata ttc gcc gac ctt tgg gca tcg att gct aca aaa tac aag    998
Asn Glu Ile Phe Ala Asp Leu Trp Ala Ser Ile Ala Thr Lys Tyr Lys
190             195                 200                 205 gat aat acg aaa att atc ttc ggc at  gtaagcgtta tatttggccg         1044
Asp Asn Thr Lys Ile Ile Phe Gly Ile
                210 tccccagtat gcactctaag ctggcacccc ag a atg aac gaa cct cat gat gtc 1098
                                    Met Asn Glu Pro His Asp Val
                                                215             220 ccc gac atc aaa atg tgg gct gca tcc gtc cag gct gct gtt aca gca   1146
Pro Asp Ile Lys Met Trp Ala Ala Ser Val Gln Ala Ala Val Thr Ala
                225                 230                 235 atc cgg aac gcc gg  gttggtggaa tttctacgag ttcgttagtt ctgcagctga   1200
Ile Arg Asn Ala Gly
240 tgtttccata g a gcg acg agc cac atc cta ctt ctt ccc ggc aac gac    1248
                Ala Thr Ser His Ile Leu Leu Leu Pro Gly Asn Asp
                            245                 250 tgg aca tct gcg gca gcc ttc atc cct aac ggc tct gcc gac gcg ctc   1296
Trp Thr Ser Ala Ala Ala Phe Ile Pro Asn Gly Ser Ala Asp Ala Leu
255                 260                 265                 270 tca aag gtc acc aac ccg gat ggc agc gtg acg aac ctt gtc ttc gac   1344
Ser Lys Val Thr Asn Pro Asp Gly Ser Val Thr Asn Leu Val Phe Asp
                275                 280                 285 gtc cac aag tat ctc gac agc gac aac agc ggc acg cac gcc gaa tgc   1392
Val His Lys Tyr Leu Asp Ser Asp Asn Ser Gly Thr His Ala Glu Cys
            290                 295                 300 gtg acg aac aat atc gcc gaa gcc tgg caa cct ctc ggg gac tgg ctc   1440
Val Thr Asn Asn Ile Ala Glu Ala Trp Gln Pro Leu Gly Asp Trp Leu
            305                 310                 315 cgt gct aat gga cgc caa gct ttc aac acc gag aca ggc ggc ggc aac   1488
Arg Ala Asn Gly Arg Gln Ala Phe Asn Thr Glu Thr Gly Gly Gly Asn
320                 325                 330 acc gca tcg tgt gta acc tat cta tgc gag cag atc gcg tac cag aat   1536
Thr Ala Ser Cys Val Thr Tyr Leu Cys Glu Gln Ile Ala Tyr Gln Asn
335                 340                 345                 350 gcc aac tcc gat g gtaagttgct ccgaagaacg tcattggcgt tgtttctgat    1589
Ala Asn Ser Asp cagtctgcag tt  tac ctc ggc tat gtt ggc tgg tca gca ggt aac ttc    1637
                Val Tyr Leu Gly Tyr Val Gly Trp Ser Ala Gly Asn Phe
                    355                 360                 365 tac cat gga tat gtc cta gac gag gtc cct aca ggg agc ggg tcg act   1685
Tyr His Gly Tyr Val Leu Asp Glu Val Pro Thr Gly Ser Gly Ser Thr
        370                 375                 380 tgg acg gac aca atg ctg gtc gct agc tgc ttg gcc ccg aac gcg gca   1733
Trp Thr Asp Thr Met Leu Val Ala Ser Cys Leu Ala Pro Asn Ala Ala
385                 390                 395 aaa tag                                                            1739
Lys
400

<210> SEQ ID NO 6
<211> LENGTH: 420
<212> TYPE: PRT
```

<213> ORGANISM: Hohenbuehelia mastrucata

<400> SEQUENCE: 6

```
Met Lys Ser Pro Tyr Phe Ala Ile Leu Leu Ala Thr Ala Leu Arg Val
-20             -15                 -10                  -5

Arg Gly Gln Gly Ala Leu Tyr Thr Gln Cys Gly Gly Val Gly Trp Thr
         -1   1              5                      10

Gly Ala Thr Thr Cys Val Ala Gly Ala Val Cys Ser Lys Leu Asn Asp
             15                  20                  25

Tyr Tyr Ser Gln Cys Ile Pro Gly Ala Ala Pro Ser Ser Ser Val
         30                  35                  40

Ser Ser Val Ser Ser Ala Ala Pro Thr Lys Val Ser Thr Ser Val
45                   50                  55                      60

Ala Ser Thr Gly Thr Thr Thr Pro Pro Thr Ala Gly Lys Leu Arg
                 65                  70                  75

Phe Thr Gly Val Asn Ile Ala Gly Phe Asp Phe Gly Cys Ser Thr Asp
             80                  85                  90

Gly Thr Cys Asn Ala Ser Gly Ala Tyr Pro Pro Leu Leu Glu Tyr Tyr
             95                 100                 105

Gly Ala Asp Gly Glu Gly Gln Met Lys His Phe Val Asn Asp Asp Gly
        110                 115                 120

Phe Asn Thr Phe Arg Leu Pro Val Gly Trp Gln Phe Leu Thr Asn Asp
125                 130                 135                 140

Val Leu Thr Gly Thr Ile Asn Glu Asp Asn Trp Val Lys Tyr Asp Ala
                145                 150                 155

Leu Val Gln Ala Cys Leu Asn Thr Gly Ala Tyr Cys Ile Val Asp Val
            160                 165                 170

His Asn Tyr Ala Arg Trp Asn Thr Lys Ile Ile Gly Gln Gly Gly Pro
        175                 180                 185

Ser Asn Glu Ile Phe Ala Asp Leu Trp Ala Ser Ile Ala Thr Lys Tyr
        190                 195                 200

Lys Asp Asn Thr Lys Ile Ile Phe Gly Ile Met Asn Glu Pro His Asp
205                 210                 215                 220

Val Pro Asp Ile Lys Met Trp Ala Ala Ser Val Gln Ala Ala Val Thr
            225                 230                 235

Ala Ile Arg Asn Ala Gly Ala Thr Ser His Ile Leu Leu Pro Gly
            240                 245                 250

Asn Asp Trp Thr Ser Ala Ala Phe Ile Pro Asn Gly Ser Ala Asp
            255                 260                 265

Ala Leu Ser Lys Val Thr Asn Pro Asp Gly Ser Val Thr Asn Leu Val
270                 275                 280

Phe Asp Val His Lys Tyr Leu Asp Ser Asp Asn Ser Gly Thr His Ala
285                 290                 295                 300

Glu Cys Val Thr Asn Asn Ile Ala Glu Ala Trp Gln Pro Leu Gly Asp
            305                 310                 315

Trp Leu Arg Ala Asn Gly Arg Gln Ala Phe Asn Thr Glu Thr Gly Gly
            320                 325                 330

Gly Asn Thr Ala Ser Cys Val Thr Tyr Leu Cys Glu Gln Ile Ala Tyr
        335                 340                 345

Gln Asn Ala Asn Ser Asp Val Tyr Leu Gly Tyr Val Gly Trp Ser Ala
        350                 355                 360

Gly Asn Phe Tyr His Gly Tyr Val Leu Asp Glu Val Pro Thr Gly Ser
365                 370                 375                 380
```

-continued

```
Gly Ser Thr Trp Thr Asp Thr Met Leu Val Ala Ser Cys Leu Ala Pro
            385                 390                 395

Asn Ala Ala Lys
        400

<210> SEQ ID NO 7
<211> LENGTH: 1960
<212> TYPE: DNA
<213> ORGANISM: Hoehenbuehelia mastrucata
<220> FEATURE:
<221> NAME/KEY: CDS
<222> LOCATION: (1)..(66)
<220> FEATURE:
<221> NAME/KEY: sig_peptide
<222> LOCATION: (1)..(57)
<220> FEATURE:
<221> NAME/KEY: mat_peptide
<222> LOCATION: (58)..()
<220> FEATURE:
<221> NAME/KEY: Intron
<222> LOCATION: (67)..(129)
<220> FEATURE:
<221> NAME/KEY: CDS
<222> LOCATION: (130)..(142)
<220> FEATURE:
<221> NAME/KEY: Intron
<222> LOCATION: (143)..(205)
<220> FEATURE:
<221> NAME/KEY: CDS
<222> LOCATION: (206)..(223)
<220> FEATURE:
<221> NAME/KEY: Intron
<222> LOCATION: (224)..(274)
<220> FEATURE:
<221> NAME/KEY: CDS
<222> LOCATION: (275)..(325)
<220> FEATURE:
<221> NAME/KEY: Intron
<222> LOCATION: (326)..(383)
<220> FEATURE:
<221> NAME/KEY: CDS
<222> LOCATION: (384)..(532)
<220> FEATURE:
<221> NAME/KEY: Intron
<222> LOCATION: (533)..(591)
<220> FEATURE:
<221> NAME/KEY: CDS
<222> LOCATION: (592)..(685)
<220> FEATURE:
<221> NAME/KEY: Intron
<222> LOCATION: (686)..(746)
<220> FEATURE:
<221> NAME/KEY: CDS
<222> LOCATION: (747)..(752)
<220> FEATURE:
<221> NAME/KEY: Intron
<222> LOCATION: (753)..(803)
<220> FEATURE:
<221> NAME/KEY: CDS
<222> LOCATION: (804)..(925)
<220> FEATURE:
<221> NAME/KEY: Intron
<222> LOCATION: (926)..(976)
<220> FEATURE:
<221> NAME/KEY: CDS
<222> LOCATION: (977)..(1093)
<220> FEATURE:
<221> NAME/KEY: Intron
<222> LOCATION: (1094)..(1142)
<220> FEATURE:
<221> NAME/KEY: CDS
<222> LOCATION: (1143)..(1263)
<220> FEATURE:
<221> NAME/KEY: Intron
<222> LOCATION: (1264)..(1316)
<220> FEATURE:
<221> NAME/KEY: CDS
```

```
<222> LOCATION: (1317)..(1418)
<220> FEATURE:
<221> NAME/KEY: Intron
<222> LOCATION: (1419)..(1470)
<220> FEATURE:
<221> NAME/KEY: CDS
<222> LOCATION: (1471)..(1523)
<220> FEATURE:
<221> NAME/KEY: Intron
<222> LOCATION: (1524)..(1572)
<220> FEATURE:
<221> NAME/KEY: CDS
<222> LOCATION: (1573)..(1682)
<220> FEATURE:
<221> NAME/KEY: Intron
<222> LOCATION: (1683)..(1739)
<220> FEATURE:
<221> NAME/KEY: CDS
<222> LOCATION: (1740)..(1888)
<220> FEATURE:
<221> NAME/KEY: Intron
<222> LOCATION: (1889)..(1940)
<220> FEATURE:
<221> NAME/KEY: CDS
<222> LOCATION: (1941)..(1957)

<400> SEQUENCE: 7 atg aaa tat att gca acc act gtg gca ctt ttt gcc gcc ctc acc tct        48
Met Lys Tyr Ile Ala Thr Thr Val Ala Leu Phe Ala Ala Leu Thr Ser
        -15                 -10                 -5 gtt cgc gcg cag caa cca gtgagtacgc aggcataatg tattcatctc               96
Val Arg Ala Gln Gln Pro
     -1  1 atcgctaata gcatattatt atgcacaaaa tag ttg tat gct caa t gtaagttcac      152
                                     Leu Tyr Ala Gln
                                          5 ctgtcagtaa tccgtgtaat aggctttctg aatatccttg gtgtgctctt cag gc          207
                                                              Cys ggt gga att gga tgg t gtacgttcaa cgtaatgtgg tcatccttac gctgtactta     263
Gly Gly Ile Gly Trp
     10 ttattcgtta g ct  gga ggg act acc tgt gtc tca gga gca tct tgc agc      312
              Ser Gly Gly Thr Thr Cys Val Ser Gly Ala Ser Cys Ser
                   15                  20                  25 aag ctg aat gac t gtgcgctgct tcgtttcgtt gccacaacat tgttacatct         365
Lys Leu Asn Asp
         30 tatctttttt cttttcag at  tat tct caa tgc ttg cct ggc gcg gct gca        415
                        Tyr Tyr Ser Gln Cys Leu Pro Gly Ala Ala Ala
                                         35                  40 ccg acc tct tcg acc ccc acc ccc act agt agt aca gga tcg tcg ccg        463
Pro Thr Ser Ser Thr Pro Thr Pro Thr Ser Ser Thr Gly Ser Ser Pro
         45                  50                  55 gca ccc acc gcc tcc agc gtg ctg cct ttt gtt ggc ggc gtc aac atg        511
Ala Pro Thr Ala Ser Ser Val Leu Pro Phe Val Gly Gly Val Asn Met
         60                  65                  70 gct ggt tac gac ttt tcc tcc gtacgttcaa acaaatgaag acaaaggtat           562
Ala Gly Tyr Asp Phe Ser Ser
         75                  80 cctgttttga actgaaggta atctttag gct acc gac ggc tcc ttc aag gac        615
                                 Ala Thr Asp Gly Ser Phe Lys Asp
                                                      85 gac agt acc gac ccg ccc gtc tct cag ttc tct cac ttt gct cag caa        663
Asp Ser Thr Asp Pro Pro Val Ser Gln Phe Ser His Phe Ala Gln Gln
         90                  95                  100
```

```
ggc gtc aac att ttc cgt att c gtgcgttcgc ctttattccg tcttatgaat      715
Gly Val Asn Ile Phe Arg Ile
105                 110 aactgactca acgacaattc gttgatgtta gcc ttt g gtacgtttag                762
                                Pro Phe tacttacctg aattgctttt gttcgttaat cgttgttgta gct tgg caa ttg atg      817
                                              Ala Trp Gln Leu Met
                                                              115 acg cct act ctt gga ggg acg att gac ccg acg ttc ttc gcc cgc tac      865
Thr Pro Thr Leu Gly Gly Thr Ile Asp Pro Thr Phe Phe Ala Arg Tyr
        120                 125                 130 gac cga act gtg caa gct gca ctg aac tcg aat tcc aag gca tac gtt      913
Asp Arg Thr Val Gln Ala Ala Leu Asn Ser Asn Ser Lys Ala Tyr Val
135                 140                 145                 150 att att gat gtt gtatgtccat cattccactt tttgcgaggt ttttattgat          965
Ile Ile Asp Val cagtcgtcaa g cac aat tac gct cgc tgg aac ggt gcc gtc att gcc caa    1015
             His Asn Tyr Ala Arg Trp Asn Gly Ala Val Ile Ala Gln
                         155                 160                 165 ggc ggt ccc act gat gcg cag tat gcc agt cta tgg tct cag ctt gca     1063
Gly Gly Pro Thr Asp Ala Gln Tyr Ala Ser Leu Trp Ser Gln Leu Ala
        170                 175                 180 gcc aag tat gcc agc aac tcg cgc ata atc gtgagtcaac gtttataggc       1113
Ala Lys Tyr Ala Ser Asn Ser Arg Ile Ile
        185                 190 tgcggttctg cttttcaat cattcgtag ttt ggc atc atg aac gag ccc cat      1166
                                Phe Gly Ile Met Asn Glu Pro His
                                                195                 200 gat gtc ccg aac atc gca act tgg gcg aac tct gtt cag gcc gca gtg     1214
Asp Val Pro Asn Ile Ala Thr Trp Ala Asn Ser Val Gln Ala Ala Val
                205                 210                 215 aac gca att cgt gcg gct ggc gca act tcg caa gtc att ctt ctt ccc g   1263
Asn Ala Ile Arg Ala Ala Gly Ala Thr Ser Gln Val Ile Leu Leu Pro
        220                 225                 230 gtacgtcgag cgcaccgttt cactgttcac aaatttcctc ataccggcgg tag gc       1318
                                                           Gly tct agc tgg tcc agc gct cag gcc ttc cct acc gaa gct ggc cct tac     1366
Ser Ser Trp Ser Ser Ala Gln Ala Phe Pro Thr Glu Ala Gly Pro Tyr
235                 240                 245                 250 ctc gtg aag gtt acg gat cct gct ggt gga acg agc aaa ctc atc ttc     1414
Leu Val Lys Val Thr Asp Pro Ala Gly Gly Thr Ser Lys Leu Ile Phe
                255                 260                 265 gat g gtaatgcaat atttactttg gactaatggc ccgaagactg actgcctgct ag     1470
Asp tc cac aag tac ctt gac agt gac aat agc ggg act cac gct gac tgt     1517
Val His Lys Tyr Leu Asp Ser Asp Asn Ser Gly Thr His Ala Asp Cys
        270                 275                 280 acg acc gtaagtcaaa actttagcat gcttaaacca ttcctcacgt gccgaatag gac  1575
Thr Thr                                                        Asp
    285 aat gtc cca gtt ttc cag aca ctc gtg aac ttc ctg aag gcc aat ggg     1623
Asn Val Pro Val Phe Gln Thr Leu Val Asn Phe Leu Lys Ala Asn Gly
            290                 295                 300 aac cgt cag gct ctc ctc agc gaa act ggc ggt ggc aac acc tca tcc     1671
Asn Arg Gln Ala Leu Leu Ser Glu Thr Gly Gly Gly Asn Thr Ser Ser
        305                 310                 315 tgc ttc act gc  gttcgtgcta gcctataacg agacttccgt atccttactc         1722
Cys Phe Thr Ala
        320
```

```
acatgttctt ataacag a ctc aat tca gaa ctt gct ttc gtc aag tca aac        1773
                    Leu Asn Ser Glu Leu Ala Phe Val Lys Ser Asn
                        325             330 ttc cca acc ctt gtg ggc ttc acg gtt tgg agt gct ggt gcc ttc gac         1821
Phe Pro Thr Leu Val Gly Phe Thr Val Trp Ser Ala Gly Ala Phe Asp
335             340                 345 aca act tac atc cta acg ctg acg ccg aat cct gac ggc tct gac caa         1869
Thr Thr Tyr Ile Leu Thr Leu Thr Pro Asn Pro Asp Gly Ser Asp Gln
350             355                 360             365 cct ctc tgg atc caa gct g gtaagcgcag ttgattctga actccaataa              1918
Pro Leu Trp Ile Gln Ala
                370 tcaagactta cgttttttttt ag tc cgc ccc aac ctg cct tga                    1960
                            Val Arg Pro Asn Leu Pro
                                    375
```

<210> SEQ ID NO 8
<211> LENGTH: 396
<212> TYPE: PRT
<213> ORGANISM: Hoehenbuehelia mastrucata

<400> SEQUENCE: 8

```
Met Lys Tyr Ile Ala Thr Thr Val Ala Leu Phe Ala Ala Leu Thr Ser
                -15             -10             -5

Val Arg Ala Gln Gln Pro Leu Tyr Ala Gln Cys Gly Gly Ile Gly Trp
        -1  1              5                   10

Ser Gly Gly Thr Thr Cys Val Ser Gly Ala Ser Cys Ser Lys Leu Asn
        15              20              25

Asp Tyr Tyr Ser Gln Cys Leu Pro Gly Ala Ala Ala Pro Thr Ser Ser
30              35              40              45

Thr Pro Thr Pro Thr Ser Ser Thr Gly Ser Ser Pro Ala Pro Thr Ala
                50              55              60

Ser Ser Val Leu Pro Phe Val Gly Gly Val Asn Met Ala Gly Tyr Asp
            65              70              75

Phe Ser Ser Ala Thr Asp Gly Ser Phe Lys Asp Asp Ser Thr Asp Pro
        80              85              90

Pro Val Ser Gln Phe Ser His Phe Ala Gln Gln Gly Val Asn Ile Phe
    95              100             105

Arg Ile Pro Phe Ala Trp Gln Leu Met Thr Pro Thr Leu Gly Gly Thr
110             115             120             125

Ile Asp Pro Thr Phe Phe Ala Arg Tyr Asp Arg Thr Val Gln Ala Ala
                130             135             140

Leu Asn Ser Asn Ser Lys Ala Tyr Val Ile Asp Val His Asn Tyr
            145             150             155

Ala Arg Trp Asn Gly Ala Val Ile Ala Gln Gly Gly Pro Thr Asp Ala
        160             165             170

Gln Tyr Ala Ser Leu Trp Ser Gln Leu Ala Ala Lys Tyr Ala Ser Asn
    175             180             185

Ser Arg Ile Ile Phe Gly Ile Met Asn Glu Pro His Asp Val Pro Asn
190             195             200             205

Ile Ala Thr Trp Ala Asn Ser Val Gln Ala Ala Val Asn Ala Ile Arg
                210             215             220

Ala Ala Gly Ala Thr Ser Gln Val Ile Leu Leu Pro Gly Ser Ser Trp
            225             230             235

Ser Ser Ala Gln Ala Phe Pro Thr Glu Ala Gly Pro Tyr Leu Val Lys
        240             245             250
```

```
Val Thr Asp Pro Ala Gly Gly Thr Ser Lys Leu Ile Phe Asp Val His
    255             260             265
Lys Tyr Leu Asp Ser Asp Asn Ser Gly Thr His Ala Asp Cys Thr Thr
270             275             280             285
Asp Asn Val Pro Val Phe Gln Thr Leu Val Asn Phe Leu Lys Ala Asn
            290             295             300
Gly Asn Arg Gln Ala Leu Leu Ser Glu Thr Gly Gly Gly Asn Thr Ser
            305             310             315
Ser Cys Phe Thr Ala Leu Asn Ser Glu Leu Ala Phe Val Lys Ser Asn
        320             325             330
Phe Pro Thr Leu Val Gly Phe Thr Val Trp Ser Ala Gly Ala Phe Asp
    335             340             345
Thr Thr Tyr Ile Leu Thr Leu Thr Pro Asn Pro Asp Gly Ser Asp Gln
350             355             360             365
Pro Leu Trp Ile Gln Ala Val Arg Pro Asn Leu Pro
            370             375
```